US010893850B2

(12) United States Patent
Gafner et al.

(10) Patent No.: US 10,893,850 B2
(45) Date of Patent: Jan. 19, 2021

(54) METHODS AND APPARATUSES FOR GUIDING COLLECTION OF ULTRASOUND DATA USING MOTION AND/OR ORIENTATION DATA

(71) Applicant: Butterfly Network, Inc., Guilford, CT (US)

(72) Inventors: Tomer Gafner, Forest Hills, NY (US); Igor Lovchinsky, New York, NY (US); Ardavan Saeedi, Jersey City, NJ (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 16/669,443

(22) Filed: Oct. 30, 2019

(65) Prior Publication Data
US 2020/0060658 A1 Feb. 27, 2020

Related U.S. Application Data

(63) Continuation of application No. 16/529,872, filed on Aug. 2, 2019.
(Continued)

(51) Int. Cl.
*A61B 8/08* (2006.01)
*A61B 90/00* (2016.01)
(Continued)

(52) U.S. Cl.
CPC ............ *A61B 8/5238* (2013.01); *A61B 5/066* (2013.01); *A61B 8/5207* (2013.01); *A61B 90/36* (2016.02);
(Continued)

(58) Field of Classification Search
CPC ... A61B 8/5238; A61B 8/5207; A61B 8/5292; A61B 90/36; A61B 90/39; A61B 5/066;
(Continued)

(56) References Cited

U.S. PATENT DOCUMENTS

| 7,867,167 B2 | 1/2011 | Boctor et al. |
| 8,756,033 B2 | 6/2014 | Ishikawa et al. |

(Continued)

FOREIGN PATENT DOCUMENTS

| WO | WO 2017/222970 A1 | 12/2017 |
| WO | WO 2018/094118 A1 | 5/2018 |

OTHER PUBLICATIONS

International Search Report and Written Opinion dated Oct. 7, 2019 in connection with International Application No. PCT/US2019/044774.

(Continued)

*Primary Examiner* — Michael T Rozanski
(74) *Attorney, Agent, or Firm* — Wolf, Greenfield & Sacks, P.C.

(57) ABSTRACT

Aspects of technology described herein relate to guiding collection of ultrasound data collection using motion and/or orientation data. A directional indicator corresponding to an instruction for moving an ultrasound imaging device relative to a subject may be displayed in an augmented reality display. The direction of the directional indicator in the augmented reality display may be independent of an orientation of the ultrasound imaging device. The augmented reality display may include video captured by a camera that depicts the ultrasound imaging device and a fiducial marker on the ultrasound imaging device. The direction of the directional indicator may be based on the pose of the camera relative to the fiducial marker and the rotation and/or tilt of the ultrasound imaging device relative to the axis of gravity. The direction of the directional indicator may also be based on the pose of the camera relative to the subject.

6 Claims, 13 Drawing Sheets

Related U.S. Application Data

(60) Provisional application No. 62/714,638, filed on Aug. 3, 2018.

(51) Int. Cl.
   *A61B 5/06* (2006.01)
   *G16H 40/63* (2018.01)

(52) U.S. Cl.
   CPC ............ *A61B 90/39* (2016.02); *A61B 8/5292* (2013.01); *A61B 2090/363* (2016.02); *A61B 2090/365* (2016.02); *A61B 2090/3925* (2016.02); *G16H 40/63* (2018.01)

(58) Field of Classification Search
   CPC ........ A61B 2090/363; A61B 2090/365; A61B 2090/3925; G16H 40/63
   See application file for complete search history.

(56) References Cited

U.S. PATENT DOCUMENTS

| | | |
|---|---|---|
| 8,852,103 B2 | 10/2014 | Rothberg et al. |
| 9,521,991 B2 | 12/2016 | Rothberg et al. |
| 9,592,030 B2 | 3/2017 | Rothberg et al. |
| 10,628,932 B2 | 4/2020 | Rothberg et al. |
| 10,702,242 B2 | 7/2020 | de Jonge et al. |
| 10,706,520 B2 | 7/2020 | Rothberg et al. |
| 2006/0176242 A1 | 8/2006 | Jaramaz et al. |
| 2011/0055447 A1 | 3/2011 | Costa |
| 2016/0331353 A1 | 11/2016 | Ralston et al. |
| 2017/0105701 A1 | 4/2017 | Pelissier et al. |
| 2017/0360397 A1 | 12/2017 | Rothberg et al. |
| 2017/0360401 A1 | 12/2017 | Rothberg et al. |
| 2017/0360402 A1 | 12/2017 | de Jonge et al. |
| 2017/0360403 A1 | 12/2017 | Rothberg et al. |
| 2017/0360404 A1 | 12/2017 | Gafner et al. |
| 2017/0360411 A1 | 12/2017 | Rothberg et al. |
| 2017/0360412 A1 | 12/2017 | Rothberg et al. |
| 2018/0132724 A1 | 5/2018 | Waechter-Stehle et al. |
| 2019/0038260 A1 | 2/2019 | Lee et al. |
| 2019/0056693 A1 | 2/2019 | Gelman et al. |
| 2019/0130554 A1 | 5/2019 | Rothberg et al. |
| 2019/0142388 A1 | 5/2019 | Gonyeau et al. |
| 2019/0196600 A1 | 6/2019 | Rothberg et al. |
| 2019/0239850 A1* | 8/2019 | Dalvin .................. A61B 90/36 |
| 2019/0261957 A1 | 8/2019 | Zaslavsky et al. |
| 2019/0266716 A1 | 8/2019 | Rothberg et al. |
| 2019/0282208 A1 | 9/2019 | Silberman et al. |
| 2019/0307428 A1 | 10/2019 | Silberman et al. |
| 2020/0037986 A1 | 2/2020 | Silberman et al. |
| 2020/0037987 A1 | 2/2020 | Silberman et al. |
| 2020/0037998 A1 | 2/2020 | Gafner et al. |
| 2020/0046322 A1 | 2/2020 | Silberman et al. |
| 2020/0054307 A1 | 2/2020 | Silberman et al. |
| 2020/0211174 A1 | 7/2020 | Rothberg et al. |
| 2020/0214672 A1 | 7/2020 | de Jonge et al. |
| 2020/0214674 A1 | 7/2020 | Gafner et al. |
| 2020/0214679 A1 | 7/2020 | Silberman et al. |
| 2020/0261054 A1 | 8/2020 | Silberman et al. |
| 2020/0289094 A1 | 9/2020 | de Jonge et al. |
| 2020/0320694 A1 | 10/2020 | Howell et al. |

OTHER PUBLICATIONS

International Search Report and Written Opinion dated Oct. 25, 2019 in connection with International Application No. PCT/US2019/044777.

International Search Report and Written Opinion dated Oct. 29, 2019 in connection with International Application No. PCT/US2019/044786.

* cited by examiner

METHODS AND APPARATUSES FOR GUIDING COLLECTION OF ULTRASOUND DATA USING MOTION AND/OR ORIENTATION DATA

CROSS-REFERENCE TO RELATED APPLICATIONS

The present application is a Continuation claiming the benefit under 35 U.S.C. § 120 of U.S. application Ser. No. 16/529,872, filed Aug. 2, 2019, and entitled "METHODS AND APPARATUSES FOR GUIDING COLLECTION OF ULTRASOUND DATA USING MOTION AND/OR ORIENTATION DATA," which is hereby incorporated herein by reference in its entirety.

U.S. application Ser. No. 16/529,872 claims the benefit under 35 USC § 119(e) of U.S. Patent Application Ser. No. 62/714,638, filed Aug. 3, 2018, and entitled "METHODS AND APPARATUSES FOR GUIDING COLLECTION OF ULTRASOUND DATA USING MOTION AND/OR ORIENTATION DATA," which is hereby incorporated herein by reference in its entirety.

FIELD

Generally, the aspects of the technology described herein relate to ultrasound data collection. Some aspects relate to guiding collection of ultrasound data using motion and/or orientation data from an ultrasound imaging device.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using an ultrasound imaging device), sound waves are reflected off the tissue, with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound devices, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, a method includes displaying, in an augmented reality display, by a processing device in operative communication with an ultrasound imaging device, a directional indicator corresponding to an instruction for moving the ultrasound imaging device relative to a subject, wherein a direction of the directional indicator in the augmented reality display is independent of an orientation of the ultrasound imaging device.

In some embodiments, the directional indicator in the augmented reality display is displayed so as to appear in the augmented reality display to be part of a real-world environment of the ultrasound imaging device. In some embodiments, the direction of the directional indicator in the augmented reality display is determined at least partially based on an object in a real-world environment of the ultrasound imaging device. In some embodiments, the direction of the directional indicator in the augmented reality display is determined at least partially based on an object coupled to the ultrasound imaging device. In some embodiments, the direction of the directional indicator in the augmented reality display is independent of an orientation of the ultrasound imaging device relative to an axis of gravity. In some embodiments, the method further includes receiving ultrasound data from the ultrasound imaging device; determining the instruction for moving the ultrasound imaging device relative to the subject based on the ultrasound data; receiving a frame of video of the ultrasound imaging device from a camera, wherein the ultrasound imaging device includes a fiducial marker coupled to the ultrasound imaging device and depicted in the frame of video; determining, based on the frame of video, a pose of the camera relative to the fiducial marker; receiving motion and/or orientation data from the ultrasound imaging device; determining, based on the motion and/or orientation data, a rotation and/or a tilt of the ultrasound imaging device relative to the axis of gravity; and determining the direction of the directional indicator in the augmented reality display based on the instruction for moving the ultrasound imaging device relative to the subject, the pose of the camera relative to the fiducial marker, and the rotation and/or tilt of the ultrasound imaging device relative to the axis of gravity.

In some embodiments, the method further includes displaying, in the augmented reality display, the directional indicator superimposed on the frame of video. In some embodiments, determining the instruction for moving the ultrasound imaging device relative to the subject includes determining a second direction relative to the subject for moving the ultrasound imaging device. In some embodiments, determining the direction of the directional indicator includes determining a third direction relative to the fiducial marker such that, when the fiducial marker is in a default orientation relative to the subject, the third direction relative to the fiducial marker is equivalent to the second relative to the subject; determining a first transformation that quantifies an inverse of the rotation and/or tilt of the ultrasound imaging device relative to the axis of gravity; applying the first transformation to the third direction relative to the fiducial marker to produce a fourth direction relative to the fiducial marker; and determining, based on the pose of the camera relative to the fiducial marker, a fifth direction in the augmented reality display that appears to point in the fourth direction relative to the fiducial marker. In some embodiments, determining the third direction relative to the fiducial marker includes determining the third direction relative to the fiducial marker in a marker coordinate system referenced to the fiducial marker. In some embodiments, determining the first transformation that quantifies the inverse of the rotation and/or tilt relative to the axis of gravity includes determining the first transformation that quantifies the inverse of the rotation and/or tilt relative to the axis of gravity in the marker coordinate system. In some embodiments, applying the first transformation to the third direction relative to the fiducial marker to produce the fourth direction relative to the fiducial marker includes multiplying the first transformation by at least two points including the third direction relative to the fiducial marker. In some embodiments, determining the fifth direction in the augmented reality display that appears to point in the fourth direction relative to the fiducial marker includes determining a second transformation quantifying a translation and/or rotation of a camera coordinate system referenced to the camera with respect to the marker coordinate system referenced to the fiducial marker; determining a third transformation quantifying a projection of the camera coordinate system onto an image coordinate system referenced to the frame of video; and applying the second transformation and the third transformation to the fourth direction relative to the fiducial marker to produce the fifth direction in the augmented reality display. In some embodiments, applying the second transformation and the third transformation to the fourth direction relative to the fiducial marker to produce the fifth direction in the augmented reality display includes multiplying the second transformation by at least two points including the fourth direction relative to the fiducial marker to produce an intermediate result; and multiplying the intermediate result by the third transformation.

In some embodiments, determining the instruction for moving the ultrasound imaging device includes inputting the ultrasound data to a statistical model configured to output instructions for moving the ultrasound imaging device based on inputted ultrasound data. In some embodiments, the ultrasound imaging device is configured to generate the motion and/or orientation data using one or more of an accelerometer, a gyroscope, or a magnetometer on the ultrasound imaging device. In some embodiments, the camera is on the processing device. In some embodiments, the fiducial marker is coupled to the ultrasound imaging device. In some embodiments, the fiducial marker includes one or more ArUco markers. In some embodiments, the fiducial marker includes a cube coupled to an end of the ultrasound imaging device. In some embodiments, the cube includes two halves configured to couple together around the end of the ultrasound imaging device. In some embodiments, the ultrasound imaging device further includes a cable; the cube includes a hole extending through the cube; and the cable extends from the end of the ultrasound imaging device through the cube.

In some embodiments, the directional indicator in the augmented reality display is displayed so as to appear in the augmented reality display to be part of a real-world environment of the ultrasound imaging device. In some embodiments, the direction of the directional indicator in the augmented reality display is determined at least partially based on an object in a real-world environment of the ultrasound imaging device. In some embodiments, the direction of the directional indicator in the augmented reality display is determined at least partially based on the subject. In some embodiments, the direction of the directional indicator in the augmented reality display is independent of an orientation of the ultrasound imaging device relative to the subject. In some embodiments, the method further includes receiving ultrasound data from the ultrasound imaging device; determining, based on the ultrasound data, the instruction for moving the ultrasound imaging device relative to the subject; receiving a frame of video of the subject from a camera; determining, based on the frame of video, a pose of the camera relative to the subject; and determining the direction of the directional indicator in the augmented reality display based on the instruction for moving the ultrasound imaging device relative to the subject and the pose of the camera relative to the subject.

In some embodiments, the method further includes displaying, in the augmented reality display, the directional indicator superimposed on the frame of video. In some embodiments, determining the instruction for moving the ultrasound imaging device relative to the subject includes determining a second direction relative to the subject for moving the ultrasound imaging device. In some embodiments, determining the direction of the directional indicator includes determining, based on the pose of the camera relative to the subject, a third direction in the augmented reality display that appears to point in the second direction relative to the subject. In some embodiments, determining the third direction in the augmented reality display that appears to point in the second direction relative to the fiducial marker includes determining a second transformation quantifying a translation and/or rotation of a camera coordinate system referenced to the camera with respect to the marker coordinate system referenced to the fiducial marker; determining a third transformation quantifying a projection of the camera coordinate system onto an image coordinate system referenced to the frame of video; and applying the second transformation and the third transformation to the second direction relative to the subject. In some embodiments, applying the second transformation and the third transformation to the second direction relative to the fiducial marker includes multiplying the second transformation by at least two points including the second direction relative to the subject to produce an intermediate result; and multiplying the intermediate result by the third transformation. In some embodiments, determining, based on the frame of video of the subject, the pose of the camera relative to the subject includes inputting the frame of video of the subject to a statistical model configured to output the pose of the camera relative to the subject based on the inputted frame of video of the subject. In some embodiments, the camera is on the processing device. In some embodiments, determining the instruction for moving the ultrasound imaging device includes inputting the ultrasound data to a statistical model configured to output instructions for moving the ultrasound imaging device based on inputted ultrasound data.

Some aspects include at least one non-transitory computer-readable storage medium storing processor-executable instructions that, when executed by at least one processor, cause the at least one processor to perform the above aspects and embodiments. Some aspects include an apparatus having a processing device configured to perform the above aspects and embodiments.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
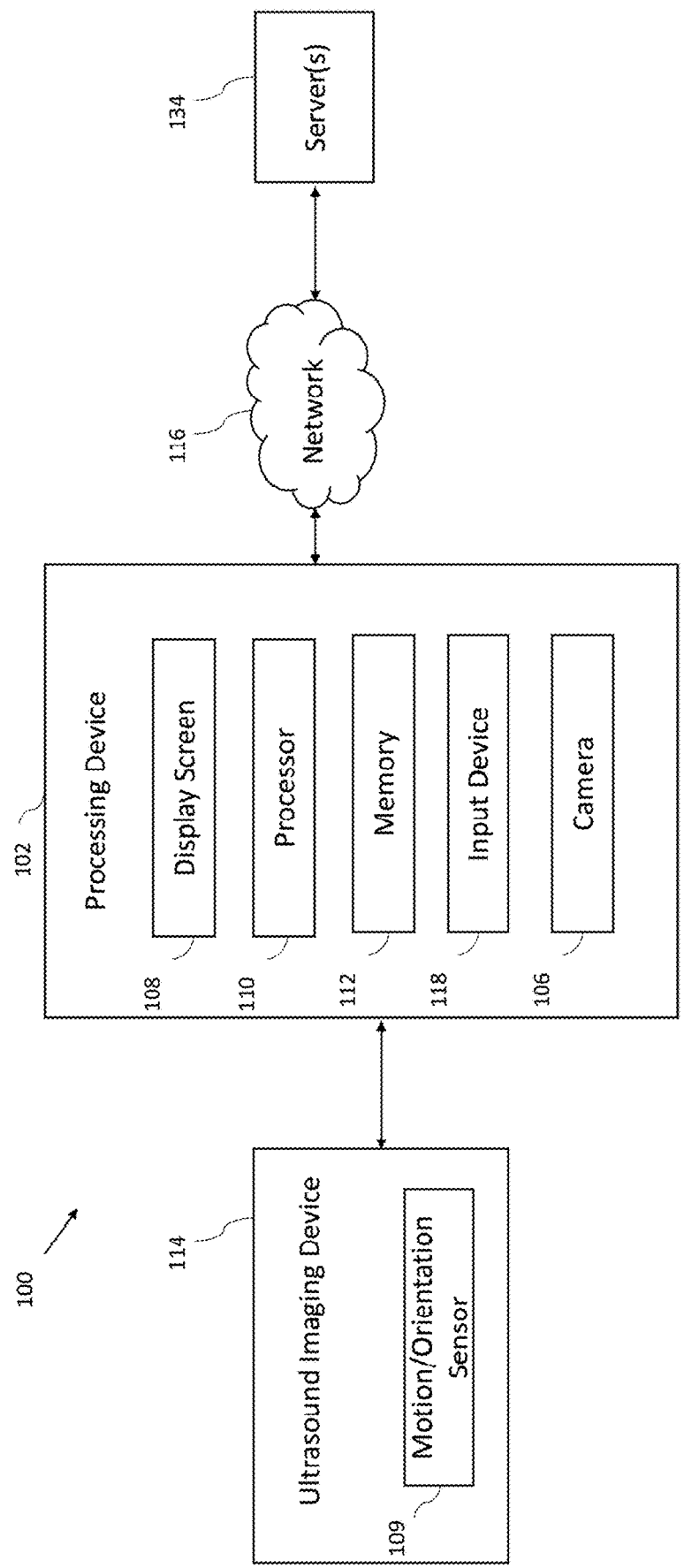
FIG. 1 illustrates a schematic block diagram of an example ultrasound system upon which various aspects of the technology described herein may be practiced.

Ultrasound examinations often include the acquisition of ultrasound images that contain a view of a particular anatomical structure (e.g., an organ) of a subject. Acquisition of these ultrasound images typically requires considerable skill. For example, an ultrasound technician operating an ultrasound device may need to know where the anatomical structure to be imaged is located on the subject and further how to properly position the ultrasound device on the subject to capture a medically relevant ultrasound image of the anatomical structure. Holding the ultrasound device a few inches too high or too low on the subject may make the difference between capturing a medically relevant ultrasound image and capturing a medically irrelevant ultrasound image. As a result, non-expert operators of an ultrasound device may have considerable trouble capturing medically relevant ultrasound images of a subject. Common mistakes by these non-expert operators include: capturing ultrasound images of the incorrect anatomical structure and capturing foreshortened (or truncated) ultrasound images of the correct anatomical structure.

Conventional ultrasound systems are large, complex, and expensive systems that are typically only purchased by large medical facilities with significant financial resources. Recently, cheaper and less complex ultrasound imaging devices have been introduced. Such imaging devices may include ultrasonic transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application), which is incorporated by reference herein in its entirety. The reduced cost and increased portability of these new ultrasound devices may make them significantly more accessible to the general public than conventional ultrasound devices.

The inventors have recognized and appreciated that although the reduced cost and increased portability of ultrasound imaging devices makes them more accessible to the general populace, people who could make use of such devices have little to no training for how to use them. For example, a small clinic without a trained ultrasound technician on staff may purchase an ultrasound device to help diagnose patients. In this example, a nurse at the small clinic may be familiar with ultrasound technology and human physiology, but may know neither which anatomical views of a patient need to be imaged in order to identify medically-relevant information about the patient nor how to obtain such anatomical views using the ultrasound device. In another example, an ultrasound device may be issued to a patient by a physician for at-home use to monitor the patient's heart. In all likelihood, the patient understands neither human physiology nor how to image his or her own heart with the ultrasound device.

Accordingly, the inventors have developed assistive ultrasound imaging technology for guiding an operator of an ultrasound device how to move the ultrasound device relative to an anatomical area of a subject in order to capture medically relevant ultrasound data. To guide the user, the processing device may output one or more instructions for moving the ultrasound imaging device from the current position and orientation to the target position and orientation. To output an instruction, the processing device may capture, using a camera, a video in real-time of the ultrasound imaging device and/or the subject, and display an augmented reality display including a directional indicator (e.g., an arrow) superimposed on the video, where the directional indicator indicates the instruction for moving the ultrasound imaging device. For example, if the instruction is to move the ultrasound imaging device in the superior direction (i.e., in the superior direction relative to the subject), the processing device may display a directional indicator in the superior direction.

The inventors have recognized that it may be helpful to couple a fiducial marker, such as a marker conforming to the ArUco library for augmented reality applications (referred to herein as an "ArUco marker") to an ultrasound imaging device. When the ultrasound imaging device is in a default orientation relative to the subject being imaged, a particular direction relative to the fiducial marker may point in a particular direction relative to the subject being imaged, such as superior to the subject. A processing device may receive video of the ultrasound imaging device and the fiducial marker coupled to the ultrasound imaging device and display an augmented reality display that includes the video. The processing device may use pose estimation techniques to determine how to display directions in the augmented reality display such that the directions appear to point in particular directions relative to the fiducial marker in the video. For example, the processing device may display a directional indicator in the augmented reality display that appears to be parallel to the direction relative to the fiducial marker that points in the superior direction relative to the subject. This directional indicator may serve as an instruction to move the ultrasound imaging device in the superior direction relative to the subject. However, once the ultrasound imaging device is rotated or tilted, this direction relative to the fiducial marker may no longer point in the superior direction relative to the subject, and displaying a directional indicator that is parallel to this direction relative to the fiducial marker may no longer be helpful as an instruction for moving the ultrasound imaging device in the superior direction. It may be helpful for directional indicators to not change direction as the ultrasound imaging device is rotated or tilted.

The inventors have recognized that to avoid directional indicators changing direction as an ultrasound imaging device is rotated or tilted, it may be helpful to fix directional indicators relative to the axis of gravity, assuming that the subject does not change orientation relative to gravity. In particular, motion and/or orientation data received from the ultrasound imaging device may be used to determine rotations and/or tilts of the ultrasound imaging device relative to the axis of gravity. When the ultrasound imaging device is in a default orientation relative to the subject being imaged, a particular direction relative to a fiducial marker (e.g., fiducial marker cube 208) that is coupled to the ultrasound imaging device may point in a particular direction relative to the subject being imaged, such as superior. The processing device may provide an instruction to move the ultrasound imaging device in that particular direction relative to the subject by displaying, on an augmented reality display, a directional indicator that appears to point in this direction relative to the fiducial marker, minus any rotation and/or tilting of the ultrasound imaging device relative to the axis of gravity from its default orientation, as indicated by the motion and/or orientation data.

The inventors have also recognized that to avoid directional indicators changing direction as an ultrasound imaging device is rotated or tilted, it may be helpful to fix directional indicators relative to the subject being imaged. In particular, a frame of video of the subject captured by a camera may be used to determine the pose of the camera relative to the subject, and the pose may be used to determine how to how to display, on an augmented reality display showing the frame of video, a directional indicator that appears to point in a particular direction relative to the subject.

According to an aspect of the present application, determination of a directional indicator to provide a user is made using a technique dependent on the orientation of the ultrasound device. For example, a magnetic flux indicator, fiducial marker, or other indicator which may be dependent on its orientation for providing location information, may be used to determine the location of the ultrasound device, which in turn may be used to determine an appropriate directional indicator to provide. However, while the determination of location of the ultrasound device may be made using an orientation-dependent technique, the directional indicator may be provided to the user independent of the orientation of the ultrasound device, such that changes in the orientation of the ultrasound device do not give rise to changes in the directional indicator unless the position of the ultrasound probe also changes.

Various aspects of the present application are described as providing or implementing statistical models. In some embodiments, a statistical model may be a convolutional neural network having one or more convolutional layers, a recurrent neural network, a fully-connected neural network, and/or any other suitable type of deep neural network model, a random forest, a support vector machine, a linear classifier, a Bayesian classifier, a non-parametric statistical model, and/or any other statistical model unless otherwise noted.

As referred to herein, a device displaying an item (e.g., a directional indicator on an augmented reality display) should be understood to mean that the device displays the item on the device's own display screen, or generates the item to be displayed on another device's display screen. To perform the latter, the device may transmit instructions to the other device for displaying the item.

As referred to herein, an augmented reality display should be understood to mean any display superimposing non-real two- or three-dimensional graphics on images/video of the real three-dimensional world such that the two- or three-dimensional graphics appear to be present in the three-dimensional world.

As referred to herein, any action performed based on some input criterion/criteria should be understood to mean that the action is performed based solely on the input criterion/criteria or based on the input criterion/criteria and other input criterion/criteria. For example, a determination made based on ultrasound data should be understood to mean that the determination is either made based on the ultrasound data or based on the ultrasound data and other input data.

As referred to herein, a pose should be understood to mean a position and/or orientation of one object relative to another object. For example, the position and/or orientation of a camera relative to a fiducial marker may be considered a pose of the camera relative to the fiducial marker.

As referred to herein, a first device that is in operative communication with a second device should be understood to mean that the first device may transmit signals to the second device and thereby affect operation of the second device. The second device may also transmit signals to the first device and thereby affect operation of the first device.

FIG. 1 illustrates a schematic block diagram of an example ultrasound system 100 upon which various aspects of the technology described herein may be practiced. The ultrasound system 100 includes an ultrasound imaging device 114, a processing device 102, a network 116, and one or more servers 134.

The ultrasound imaging device 114 includes a motion and/or orientation sensor 109. The processing device 102 includes a camera 106, a display screen 108, a processor 110, a memory 112, an input device 118, and a motion and/or orientation sensor 109. The processing device 102 is in wired (e.g., through a lightning connector or a mini-USB connector) and/or wireless communication (e.g., using BLUETOOTH, ZIGBEE, and/or WiFi wireless protocols) with the ultrasound imaging device 114. The processing device 102 is in wireless communication with the one or more servers 134 over the network 116.

The ultrasound imaging device 114 may be configured to generate ultrasound data that may be employed to generate an ultrasound image. The ultrasound imaging device 114 may be constructed in any of a variety of ways. In some embodiments, the ultrasound imaging device 114 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound imaging device 114 may include one or more ultrasonic transducers monolithically integrated onto a single semiconductor die. The ultrasonic transducers may include, for example, one or more capacitive micromachined ultrasonic transducers (CMUTs), one or more piezoelectric micromachined ultrasonic transducers (PMUTs), and/or one or more other suitable ultrasonic transducer cells. In some embodiments, the ultrasonic transducers may be formed from or on the same chip as other electronic components (e.g., transmit circuitry, receive circuitry, control circuitry, power management circuitry, and processing circuitry) to form a monolithic ultrasound device. The ultrasound imaging device 114 may transmit ultrasound data and/or ultrasound images to the processing device 102 over a wired (e.g., through a lightning connector or a mini-USB connector) and/or wireless (e.g., using BLUETOOTH, ZIGBEE, and/or WiFi wireless protocols) communication link.

The motion and/or orientation sensor 109 may be configured to generate motion and/or orientation data regarding the ultrasound imaging device 114. For example, the motion and/or orientation sensor 109 may be configured to generate to generate data regarding acceleration of the ultrasound imaging device 114, data regarding angular velocity of the ultrasound imaging device 114, and/or data regarding magnetic force acting on the ultrasound imaging device 114 (which, due to the magnetic field of the earth, may be indicative of orientation relative to the earth). The motion and/or orientation sensor 109 may include an accelerometer, a gyroscope, and/or a magnetometer. Depending on the sensors present in the motion and/or orientation sensor 109, the motion and/or orientation data generated by the motion and/or orientation sensor 109 may describe three degrees of freedom, six degrees of freedom, or nine degrees of freedom for the ultrasound imaging device 114. For example, the motion and/or orientation sensor may include an accelerometer, a gyroscope, and/or magnetometer. Each of these types of sensors may describe three degrees of freedom. If the motion and/or orientation sensor includes one of these sensors, the motion and/or orientation sensor may describe three degrees of freedom. If the motion and/or orientation sensor includes two of these sensors, the motion and/or orientation sensor may describe two degrees of freedom. If the motion and/or orientation sensor includes three of these sensors, the motion and/or orientation sensor may describe nine degrees of freedom. The ultrasound imaging device 114 may transmit motion and/or orientation data to the processing device 102 over a wired (e.g., through a lightning connector or a mini-USB connector) and/or wireless (e.g., using BLUETOOTH, ZIGBEE, and/or WiFi wireless protocols) communication link.

Referring now to the processing device 102, the processor 110 may include specially-programmed and/or special-purpose hardware such as an application-specific integrated circuit (ASIC). For example, the processor 110 may include one or more graphics processing units (GPUs) and/or one or more tensor processing units (TPUs). TPUs may be ASICs specifically designed for machine learning (e.g., statistical). The TPUs may be employed to, for example, accelerate the inference phase of a neural network. The processing device 102 may be configured to process the ultrasound data received from the ultrasound imaging device 114 to generate ultrasound images for display on the display screen 108. The processing may be performed by, for example, the processor 110. The processor 110 may also be adapted to control the acquisition of ultrasound data with the ultrasound imaging device 114. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing device 102 may be configured to perform certain of the processes described herein using the processor 110 (e.g., one or more computer hardware processors) and one or more articles of manufacture that include non-transitory computer-readable storage media such as the memory 112. The processor 110 may control writing data to and reading data from the memory 112 in any suitable manner. To perform certain of the processes described herein, the processor 110 may execute one or more processor-executable instructions stored in one or more non-transitory computer-readable storage media (e.g., the memory 112), which may serve as non-transitory computer-readable storage media storing processor-executable instructions for execution by the processor 110. The camera 106 may be configured to detect light (e.g., visible light) to form an image. The display screen 108 may be configured to display images and/or videos, and may be, for example, a liquid crystal display (LCD), a plasma display, and/or an organic light emitting diode (OLED) display on the processing device 102. The input device 118 may include one or more devices capable of receiving input from a user and transmitting the input to the processor 110. For example, the input device 118 may include a keyboard, a mouse, a microphone, touch-enabled sensors on the display screen 108, and/or a microphone. The display screen 108, the input device 118, the camera 106, and the speaker 109 may be communicatively coupled to the processor 110 and/or under the control of the processor 110.

It should be appreciated that the processing device 102 may be implemented in any of a variety of ways. For example, the processing device 102 may be implemented as a handheld device such as a mobile smartphone or a tablet. Thereby, a user of the ultrasound imaging device 114 may be able to operate the ultrasound imaging device 114 with one hand and hold the processing device 102 with another hand. In other examples, the processing device 102 may be implemented as a portable device that is not a handheld device, such as a laptop. In yet other examples, the processing device 102 may be implemented as a stationary device such as a desktop computer. The processing device 102 may be connected to the network 116 over a wired connection (e.g., via an Ethernet cable) and/or a wireless connection (e.g., over a WiFi network). The processing device 102 may thereby communicate with (e.g., transmit data to) the one or more servers 134 over the network 116. For further description of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application).

FIG. 1 should be understood to be non-limiting. For example, the ultrasound system 100 may include fewer or more components than shown and the processing device 102 may include fewer or more components than shown.

The inventors have recognized that it may be helpful to couple an orientation-dependent market to an ultrasound imaging device. A non-limiting example of an orientation-dependent marker is a fiducial marker, such as a marker conforming to the ArUco library for augmented reality applications (referred to herein as an "ArUco marker"). When the ultrasound imaging device is in a default orientation relative to the subject being imaged, a particular direction relative to the orientation-dependent marker may point in a particular direction relative to the subject being imaged, such as superior to the subject. A processing device may receive video of the ultrasound imaging device and the orientation-dependent marker coupled to the ultrasound imaging device and display an augmented reality display that includes the video. The processing device may use pose estimation techniques to determine how to display directions in the augmented reality display such that the directions appear to point in particular directions relative to the orientation-dependent marker in the video. As an example, the processing device may display a directional indicator (e.g., an arrow) in the augmented reality display that appears to be parallel to the direction relative to the orientation-dependent marker that points in the superior direction relative to the subject. In some embodiments, a directional indicator may include an instruction for translating the ultrasound imaging device in a particular direction, as opposed to an orientation indicator which may include an instruction for orienting (e.g., rotating and/or tilting) the ultrasound imaging device. The directional indicator may serve as an instruction to move the ultrasound imaging device in the superior direction relative to the subject. However, once the ultrasound imaging device is rotated or tilted, this direction relative to the orientation-dependent marker may no longer point in the superior direction relative to the subject, and displaying a directional indicator that is parallel to this direction relative to the orientation-dependent marker may no longer be helpful as an instruction for moving the ultrasound imaging device in the superior direction. It may be helpful for directional indicators to not change direction as the ultrasound imaging device is rotated or tilted.

Generally, the directional indicator in the augmented reality display may be displayed so as to appear in the augmented reality display to be part of a real-world environment of the ultrasound imaging device. To accomplish this, the direction of the directional indicator in the augmented reality display may be determined at least partially based on an object in the real-world environment of the ultrasound imaging device. For example, the direction may be determined based on an object coupled to the ultrasound imaging device, such as a fiducial marker or other orientation-dependent marker, and/or based on the subject being imaged.

Figure 2:
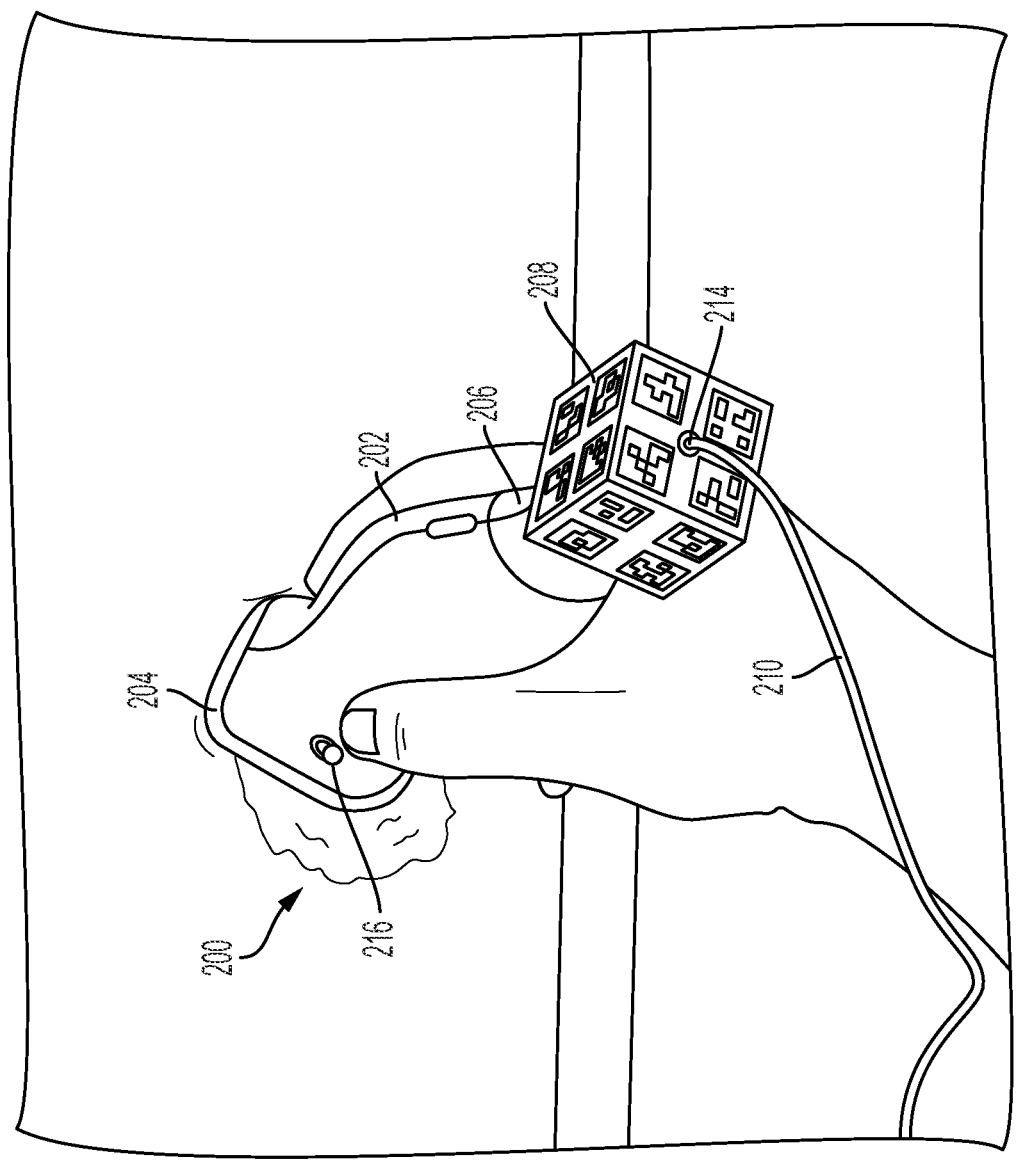
FIG. 2 illustrates an example of an ultrasound imaging device including a fiducial marker, in accordance with certain embodiments described herein.

FIG. 2 illustrates an example of an ultrasound imaging device 200 including a fiducial marker, in accordance with certain embodiments described herein. The ultrasound imaging device 200 includes a body 202 having a first end 204 and a second end 206, a fiducial marker 208, a cable 210, and an orientation marking 216. An ultrasound sensor (not visible in FIG. 2) is disposed at the first end 204. The fiducial marker 208 is coupled to the second end 206 of the body 202. The fiducial marker 208 is a cube including a plurality of markers disposed on the five surfaces of the fiducial marker 208 that do not face the second end 206 of the body 202. The face of the fiducial marker 208 facing away from the second end 206 of the body 202 includes a hole 214. The cable 210 extends from the second end 206 of the body 202 through the hole 214. The cable 210 may transmit electrical signals from the ultrasound imaging device 200 to the external processing device. The orientation marking 216 may be used by a user to orient the ultrasound imaging device in a default orientation, as will be described further below.

Figure 3:
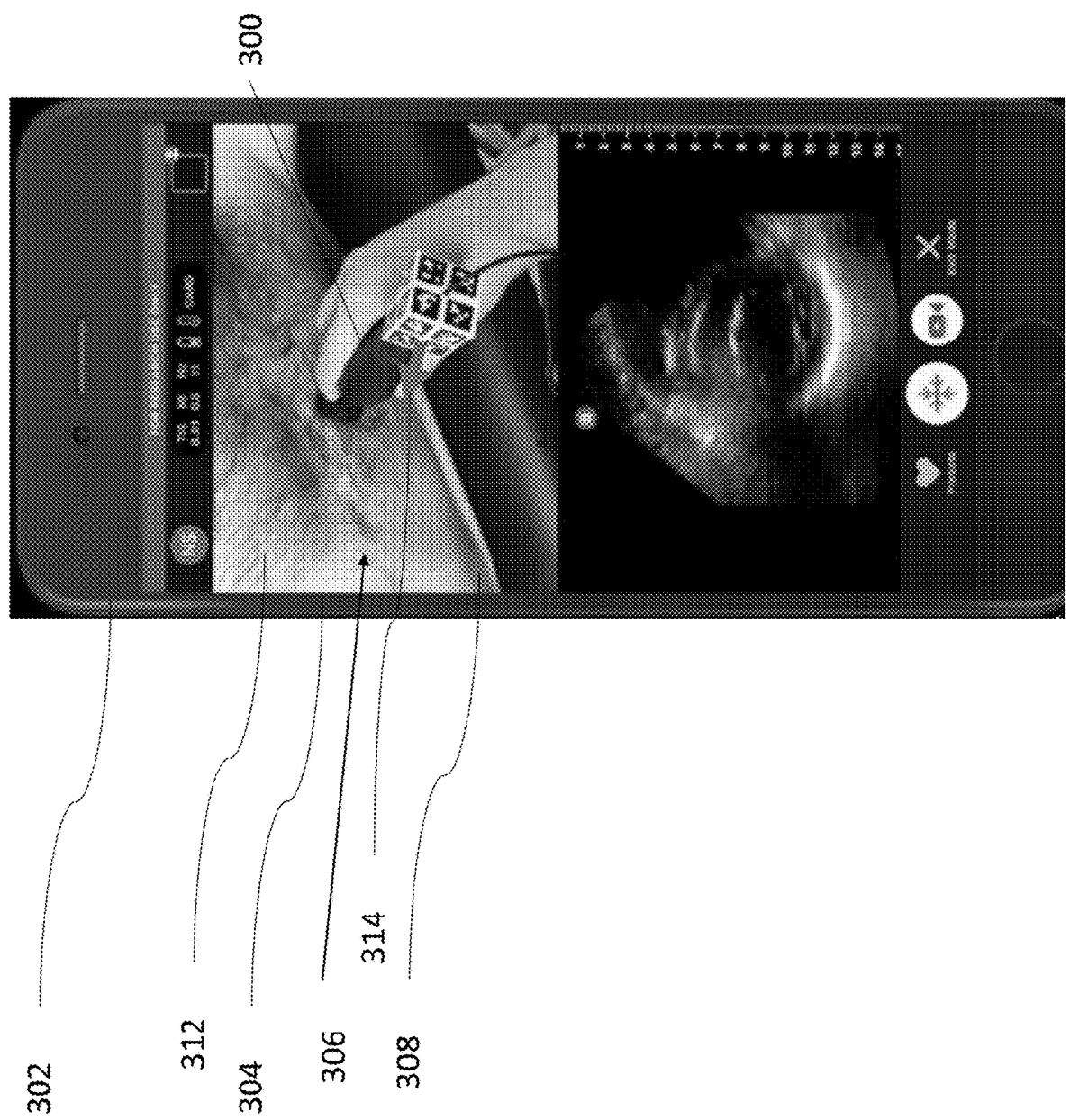
FIG. 3 illustrates an example augmented reality display including a directional indicator indicating an instruction for moving an ultrasound imaging device, in accordance with certain embodiments described herein.
Figure 4:
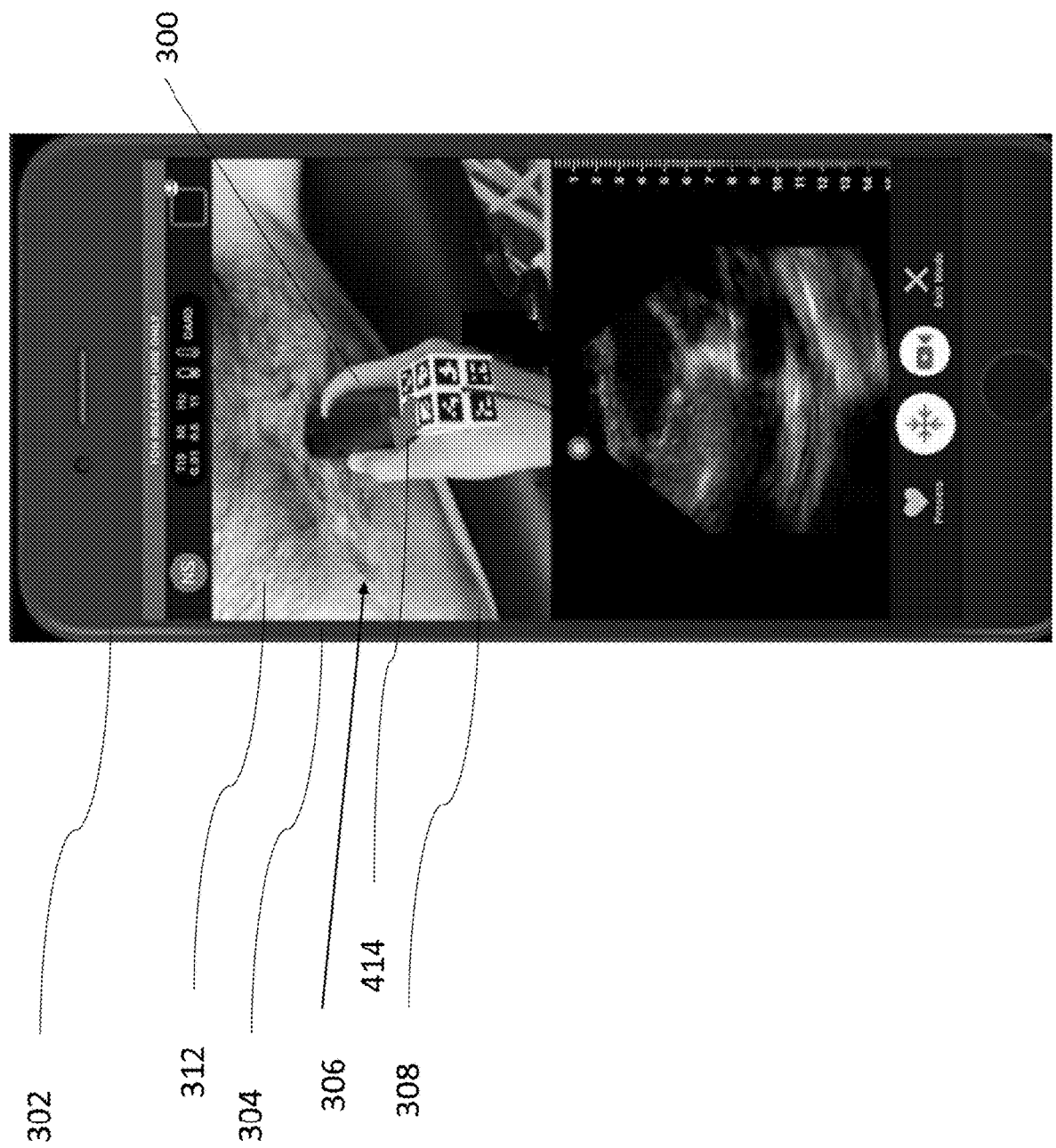
FIG. 4 illustrates the example augmented reality display of FIG. 3 including the same instruction after the ultrasound imaging device has been rotated/tilted, in accordance with certain embodiments described herein.

FIGS. 3 and 4 illustrate an example of desired operation in accordance with certain embodiments described herein. FIG. 3 illustrates an example augmented reality display including a directional indicator indicating an instruction for moving an ultrasound imaging device, and FIG. 4 illustrates the example augmented reality display including the same instruction after the ultrasound imaging device has been rotated/tilted, in accordance with certain embodiments described herein. FIGS. 3 and 4 show a processing device 302 having a display screen 304 that displays an augmented reality display 306. The augmented reality display 306 includes a video 308 of an ultrasound imaging device 300 imaging a subject 312. The augmented reality display 306 further depicts a directional indicator 314 displayed by the processing device 302 and intended to instruct a user to move the ultrasound imaging device 300 to a target position and orientation relative to the subject 312. In FIG. 4, the ultrasound imaging device 300 has been rotated compared with the orientation of ultrasound imaging device 300 in FIG. 3. The augmented reality display 306 depicts a directional indicator 414 corresponding to the same instruction as the directional indicator 314, and the direction of the directional indicator 414 has not rotated with the ultrasound imaging device 310 compared with the orientation of the directional indicator 314.

The inventors have recognized that to avoid directional indicators changing direction as an ultrasound imaging device (e.g., the ultrasound imaging device 200) is rotated or tilted, it may be helpful to fix directional indicators relative to the axis of gravity, assuming that the subject does not change orientation relative to gravity. In particular, motion and/or orientation data received from the ultrasound imaging device may be used to determine rotations and/or tilts of the ultrasound imaging device relative to the axis of gravity. When the ultrasound imaging device is in a default orientation relative to the subject being imaged, a particular direction relative to a fiducial marker (e.g., fiducial marker cube 208) that is coupled to the ultrasound imaging device may point in a particular direction relative to the subject being imaged, such as superior. The processing device may provide an instruction to move the ultrasound imaging device in that particular direction relative to the subject by displaying, on an augmented reality display, a directional indicator that appears to point in this direction relative to the fiducial marker, minus any rotation and/or tilting of the ultrasound imaging device relative to the axis of gravity from its default orientation, as indicated by the motion and/or orientation data.

Figure 5:
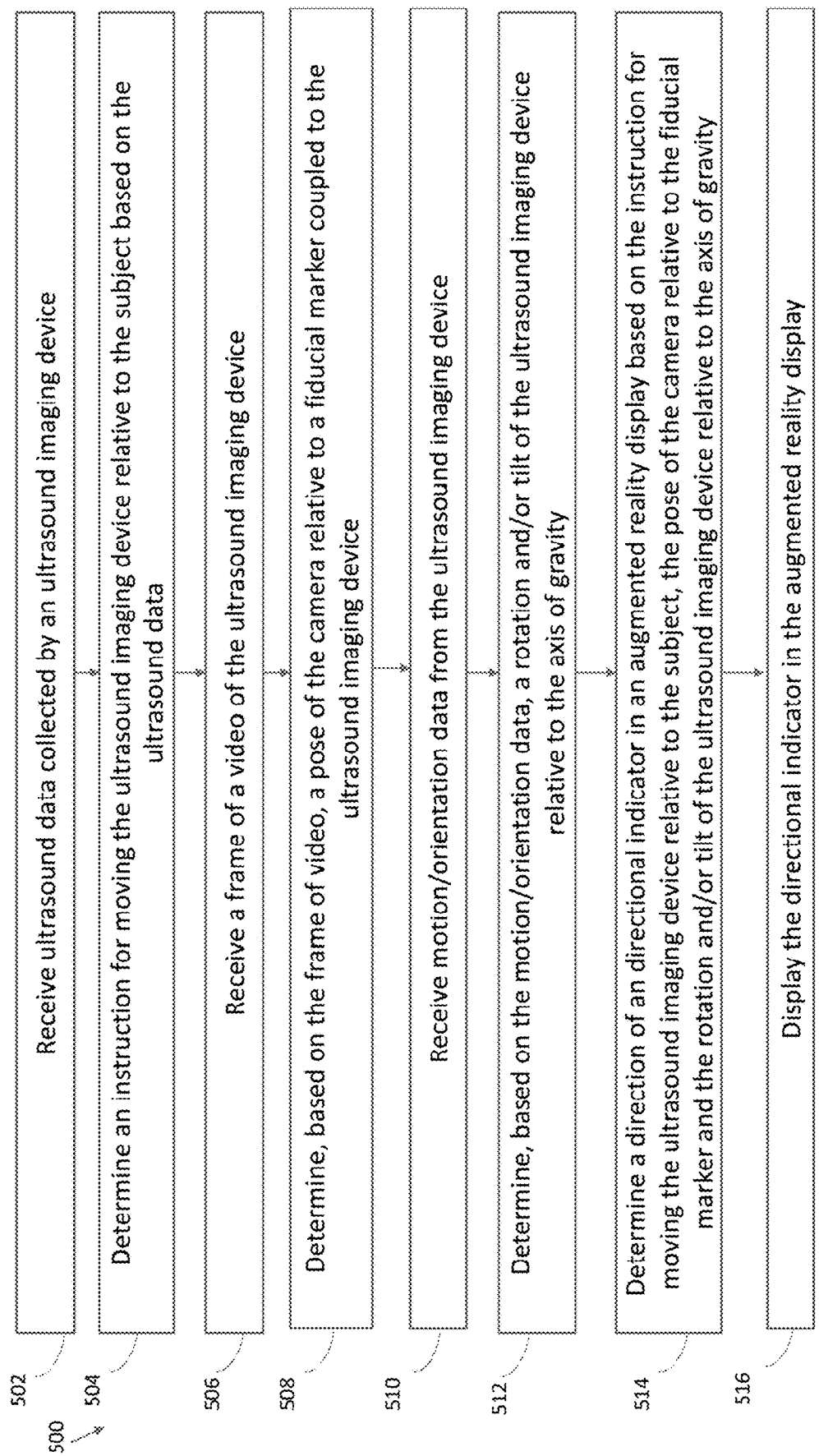
FIG. 5 illustrates an example process for guiding collection of ultrasound data, in accordance with certain embodiments described herein.

FIG. 5 illustrates an example process 500 for guiding collection of ultrasound data, in accordance with certain embodiments described herein. In some embodiments, guiding collection of ultrasound data may be performed by displaying, on an augmented reality display, a directional indicator indicating an instruction for moving an ultrasound imaging device (e.g., the ultrasound imaging device 114), where the direction of the directional indicator does not change substantially in response to movement of the ultrasound imaging device. In some embodiments, guiding collection of ultrasound data may be performed by displaying, on an augmented reality display, a directional indicator indicating an instruction for moving an ultrasound imaging device (e.g., the ultrasound imaging device 114), where the direction of the directional indicator is independent of an orientation of the ultrasound imaging device. The process 500 includes fixing, to the axis of gravity, directional indicators indicating instructions for moving the ultrasound imaging device. The process 500 may be performed by a processing device (e.g., the processing device 102) in an ultrasound system (e.g., the ultrasound system 100). The processing device may be, for example, a mobile phone, tablet, laptop, or server, and may be in operative communication with the ultrasound imaging device.

In act 502, the processing device receives ultrasound data collected from a subject by the ultrasound imaging device. The ultrasound data may include, for example, raw acoustical data, scan lines generated from raw acoustical data, or ultrasound images generated from raw acoustical data. In some embodiments, the ultrasound imaging device may generate scan lines and/or ultrasound images from raw acoustical data and transmit the scan lines and/or ultrasound images to the processing device. In other embodiments, the ultrasound imaging device may transmit the raw acoustical data to the processing device and the processing device may generate the scan lines and/or ultrasound images from the raw acoustical data. In still other embodiments, the ultrasound imaging device may generate scan lines from the raw acoustical data, transmit the scan lines to the processing device, and the processing device may generate ultrasound images from the scan lines. The ultrasound imaging device may transmit the motion and/or orientation data over a wired communication link (e.g., over Ethernet, a Universal Serial Bus (USB) cable or a Lightning cable) or over a wireless communication link (e.g., over a BLUETOOTH, WiFi, or ZIGBEE wireless communication link) to the processing device. The process 500 proceeds from act 502 to act 504.

In act 504, the processing device determines an instruction for moving the ultrasound imaging device relative to the subject based on the ultrasound data collected in act 502. In some embodiments, the processing device may input the ultrasound data received in act 502 to a statistical model configured to accept ultrasound data and output an instruction for moving the ultrasound imaging device based on the ultrasound data. The instruction may include an instruction for moving the ultrasound imaging device to a target position and/or orientation (e.g., relative to a subject being imaged) and may include any combination of instructions to translate, rotate, and tilt the ultrasound imaging device. The target position and/or orientation of the ultrasound imaging device may be a position and/or orientation of the ultrasound imaging device relative to a subject such that the ultrasound imaging device can collect a target anatomical view (e.g., a parasternal long axis view of the heart).

In some embodiments, the statistical model may be configured through training to accept ultrasound data and output an instruction for moving the ultrasound imaging device to a target pose based on the ultrasound data. In particular, the statistical model may be trained on sets of training data, where each set of training data includes ultrasound data collected from a subject when the ultrasound imaging device is at a particular pose relative to a subject, and a label indicating an instruction for moving the ultrasound imaging device from the particular pose to the target pose. The training data may be labeled manually by an annotator (e.g., a doctor, sonographer, or other medical professional). The statistical model may thereby learn what instruction to provide based on inputted ultrasound data. The statistical model may be a convolutional neural network, a random forest, a support vector machine, a linear classifier, and/or any other statistical models. For further description of statistical models and techniques, see the description with reference to FIG. 13.

In some embodiments, the statistical model may be stored in memory on the processing device and accessed internally by the processing device. In other embodiments, the statistical model may be stored in memory on another device, such as a remote server, and the processing device may transmit the motion and/or orientation data and the ultrasound data to the external device. The external device may input the ultrasound data to the statistical model and transmit the instruction outputted by the statistical model back to the processing device. Transmission between the processing device and the external device may be over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The process 500 proceeds from act 504 to act 506.

In act 506, the processing device receives a frame of video of the ultrasound imaging device captured by a camera. In some embodiments, a camera (e.g., camera 106) on the processing device may capture the frame of video. A user of the processing device may hold the ultrasound imaging device on the subject being imaged and position the camera of the processing device (which the user may also be holding) such that the ultrasound imaging device is in view of the camera. The process 500 proceeds from act 506 to act 508.

In act 508, the processing device determines, based on the frame of video received in act 506, a pose of the camera relative a fiducial marker coupled to the ultrasound imaging device. For example, the fiducial marker may be a fiducial marker cube (e.g., fiducial marker 208) coupled to one end of the ultrasound imaging device. The pose of the camera relative to the fiducial marker may be a quantification of a translation and/or rotation of the camera relative to the fiducial marker. In particular, the pose may be a quantification of a translation and/or rotation of a coordinate system referenced to the camera with respect to a coordinate system referenced to the fiducial marker, as will be discussed further below. The processing device may use pose estimation techniques, such as detecting known points on the fiducial marker (e.g., corners) in the frame of video, to determine the pose of the camera relative to the fiducial marker. The process 500 proceeds from act 508 to act 506.

In act 510, the processing device receives motion and/or orientation data from the ultrasound imaging device. For example, the motion and/or orientation data may include data regarding acceleration of the object, data regarding angular velocity of the object, and/or data regarding magnetic force acting on the object (which, due to the magnetic field of the earth, may be indicative of orientation relative to the earth). The ultrasound imaging device may include an accelerometer, a gyroscope, and/or a magnetometer, and these devices may be used by the ultrasound imaging device to generate the motion and/or orientation data. Depending on the devices used to generate the motion and/or orientation data, the motion and/or orientation data may describe three degrees of freedom, six degrees of freedom, or nine degrees of freedom for the ultrasound imaging device. The ultrasound imaging device may transmit the motion and/or orientation data over a wired communication link (e.g., over Ethernet, a Universal Serial Bus (USB) cable or a Lightning cable) or over a wireless communication link (e.g., over a BLUETOOTH, WiFi, or ZIGBEE wireless communication link) to the processing device. The process 500 proceeds from act 510 to act 512.

In act 512, the processing device determines, based on the motion and/or orientation data received in act 506, a rotation and/or tilt of the ultrasound imaging device relative to the axis of gravity. In particular, the processing device may use data from an accelerometer to determine the rotation and/or tilt of the ultrasound imaging device relative to the axis of gravity. The process 500 proceeds from act 512 to act 514.

In act 514, the processing device determines the direction of a directional indicator in an augmented reality display. The directional indicator may correspond to the instruction for moving the ultrasound imaging device determined in act 504 by pointing in a direction on the augmented reality display that matches the instruction. For example, if the instruction is to move the ultrasound imaging device in the superior direction relative to the subject, the directional indicator may point in the superior direction relative to the subject. The augmented reality display may include the frame of video of the ultrasound imaging device and a directional indicator superimposed on the frame of video, where the directional indicator corresponds to the instruction for moving the ultrasound imaging device. As will be described further below, the processing device determines the direction of the directional indicator in the augmented reality display based on the instruction for moving the ultrasound imaging device determined in act 504, the pose of the camera relative to the fiducial marker determined in act 508, and the rotation and/or tilt of the ultrasound imaging device relative to the axis of gravity determined in act 512. In some embodiments, the processing device may determine the direction such that the direction of the directional indicator in the augmented reality display does not change substantially in response to movement of the ultrasound imaging device relative to the axis of gravity. In some embodiments, the processing device may determine the direction such that the direction of the directional indicator in the augmented reality is independent of an orientation of the ultrasound imaging device relative to the axis of gravity. The process 500 proceeds from act 514 to act 516.

In act 516, the processing device displays the directional indicator in the augmented reality display. The augmented reality display may include the frame of video received in act 506, or a frame of video received later. The directional indicator may be superimposed on the frame of video with the direction determined in act 514. The processing device may display the directional indicator in the augmented reality display either on a display screen included in the processing device (e.g., display screen 108) or on a display screen on another processing device.

For example, consider an ultrasound imaging device that is oriented in a default orientation relative to the subject such that a particular direction relative to a fiducial marker coupled to the ultrasound imaging device is facing the superior direction relative to the subject. If an instruction is to move the ultrasound imaging device in the superior direction relative to the subject, the processing device may display, in an augmented reality display, a directional indicator that appears to point in that particular direction relative to the fiducial marker. If the ultrasound imaging device is rotated 90 degrees counterclockwise about the axis of gravity, the particular direction relative to the fiducial marker that originally faced the superior direction now faces the right side of the patient. The processing device may detect the 90-degree counterclockwise rotation relative to the axis of gravity, subtract a 90-degree counterclockwise rotation from the particular relative to the fiducial marker direction, and display the directional indicator in this direction. Accordingly, despite the rotation of the ultrasound imaging device, the direction of the directional indicator may remain substantially unchanged. This operation may conform to the operation shown in FIGS. 3 and 4.

Figure 6:
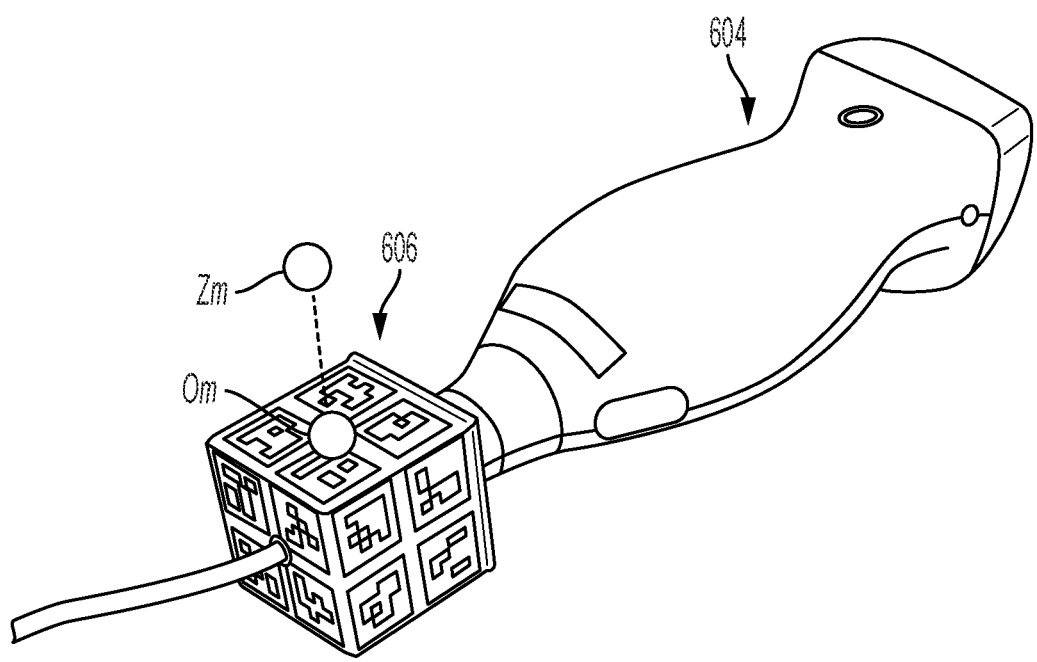
FIG. 6 illustrates an example ultrasound imaging device, an example fiducial marker coupled to the ultrasound imaging device, and particular points in a coordinate system referenced to the fiducial marker, in accordance with certain embodiments described herein.

FIG. 6 illustrates an example ultrasound imaging device 604 and an example fiducial marker 606 coupled to the ultrasound imaging device 604. In accordance with certain embodiments described herein, a three-dimensional coordinate system may referenced to the fiducial marker 606 and may be called the marker coordinate system. For example, two axes of the marker coordinate system may be in the plane of the top face of the fiducial marker 606, and the third axis of the marker coordinate system may be orthogonal to the top face of the fiducial marker 606. FIG. 6 further highlights points $O_m$ and $Z_m$, which have particular coordinates in the marker coordinate system.

Figure 7:
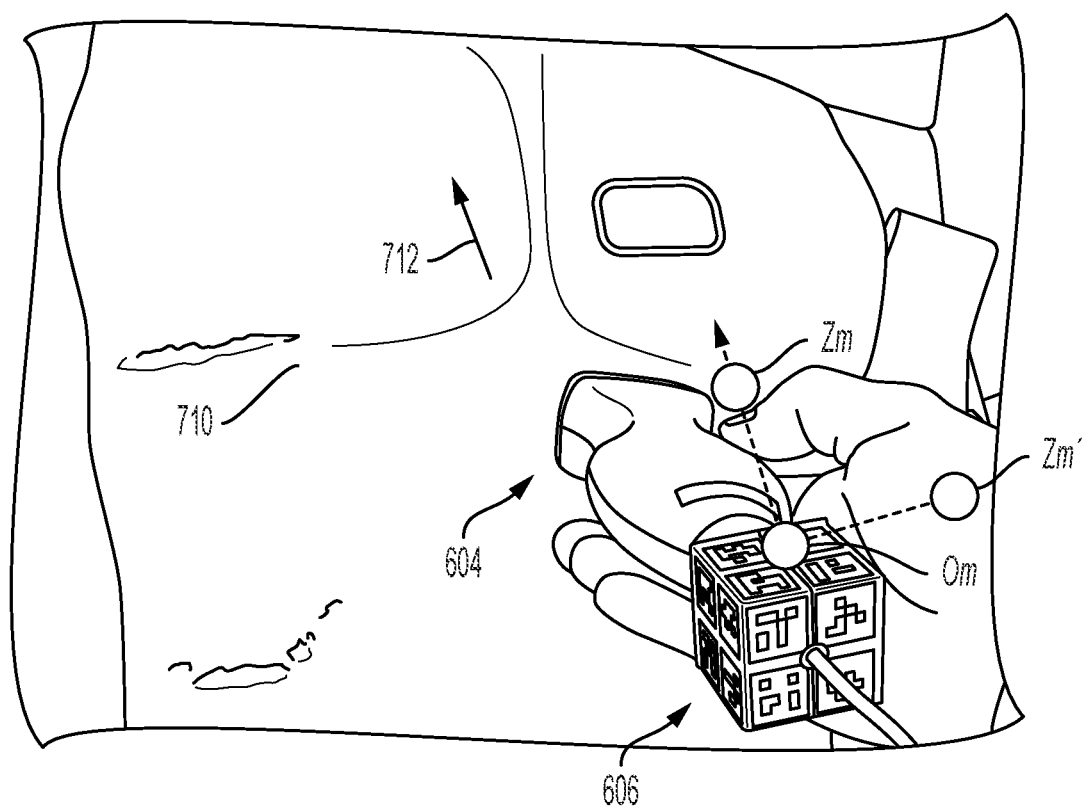
FIG. 7 illustrates the ultrasound imaging device of FIG. 6 in an example default orientation relative to a subject being imaged, in accordance with certain embodiments described herein.

FIG. 7 illustrates the ultrasound imaging device 604 in an example default orientation relative to a subject 710 being imaged, in accordance with certain embodiments described herein. When the ultrasound imaging device 604 is in the default orientation relative to the subject 710, the points $O_m$ and $Z_m$ in the marker coordinate system may define a direction $\overrightarrow{O_m Z_m}$ relative to the fiducial marker 606 that points in (i.e., is equivalent to) the superior direction 712 relative to the patient. The point $Z_m'$ will be discussed further hereinafter.

Figure 8:
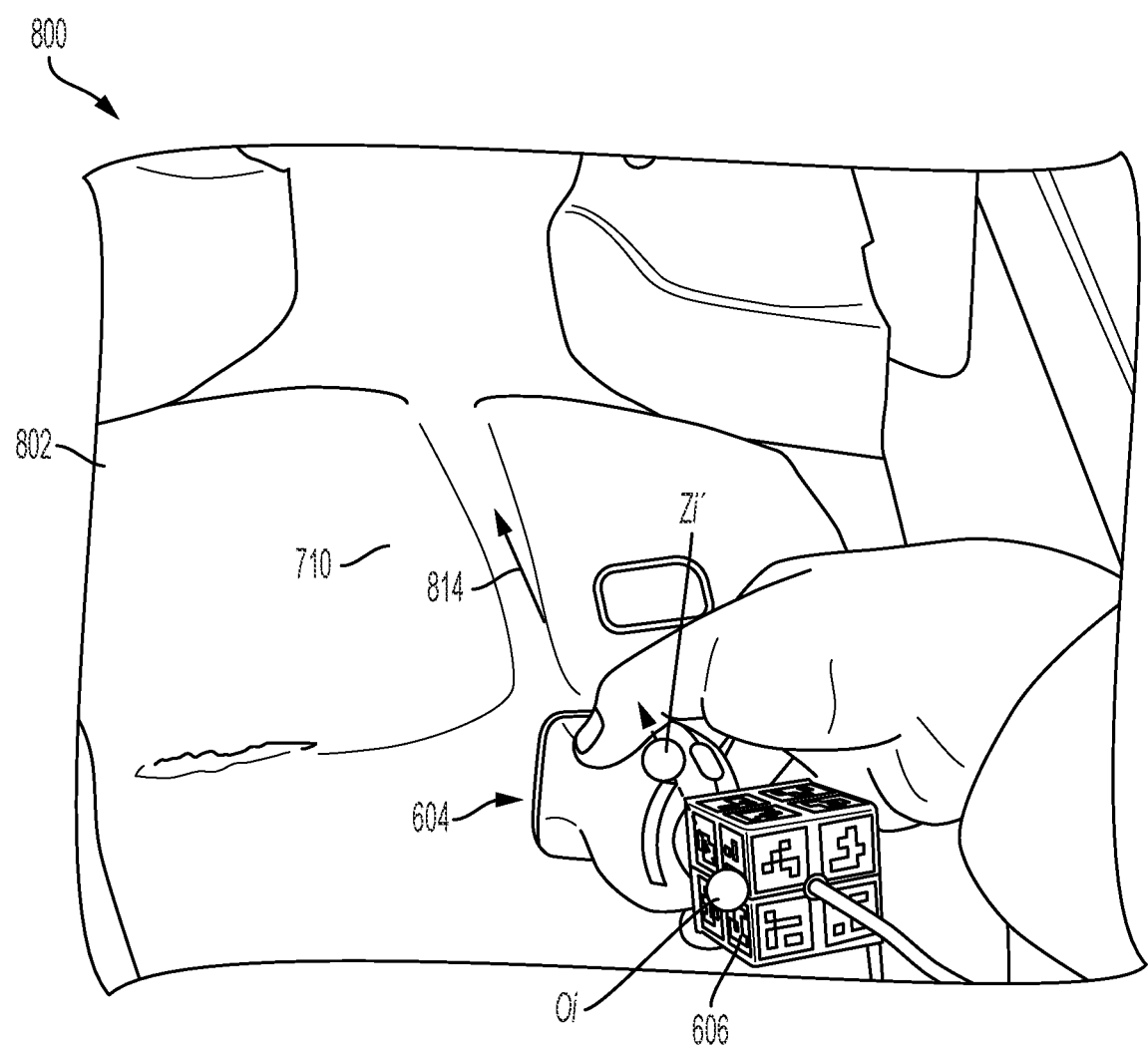
FIG. 8 illustrates an example augmented reality display including a frame of video depicting the ultrasound imaging device of and the fiducial marker of FIG. 6, in accordance with certain embodiments described herein.

FIG. 8 illustrates an example augmented reality display 800 including a frame of video 802 depicting the ultrasound imaging device 604 and the fiducial marker 606, in accordance with certain embodiments described herein. In the frame of video 802, the fiducial marker 606 has been rotated/tilted relative to the direction of gravity from the default orientation relative to the subject 710 of FIG. 7. The processing device may use motion and/or orientation data from the ultrasound imaging device 604 to determine the rotation/tilt of the ultrasound imaging device 604 relative to the direction of gravity in the marker coordinate system. Based on the rotation/tilt of the ultrasound imaging device 604 relative to the direction of gravity, the processing device may determine a rotation/tilt transformation that causes points in the marker coordinate system to be rotated and/or tilted by the inverse of the rotation/tilt of the ultrasound imaging device 604 relative to the direction of gravity. For example, if the rotation/tilt of the ultrasound imaging device 604 is a 90-degree clockwise rotation relative to the direction of gravity, the rotation/tilt transformation may quantify how to rotate points in the marker coordinate by 90-degrees counterclockwise relative to the direction of gravity. The rotation/tilt transformation may be, for example, in the form of a matrix or a quaternion.

Returning to FIG. 7, the point $Z_m'$ in the marker coordinate system may represent the point $Z_m$ rotated/tilted by the same rotation/tilt of the ultrasound imaging device 604 in FIG. 8 relative to the default orientation of the ultrasound imaging device 604 in FIG. 7. In particular, the point $Z_m'$ may represent the result of applying the rotation/tilt transformation to the point $Z_m$ (e.g., multiplying the points $O_m'$ and $Z_m'$ by the rotation/tilt transformation if the rotation/tilt transformation is a matrix). (In the example of FIG. 7, the point $Z_m$ is transformed to point $Z_m'$ but the point $O_m$ is at the origin of the marker coordinate system and does not change when rotated/tilted by the rotation/tilt image transformation.)

Returning to FIG. 8, the camera that captured the frame of video 802 may have its own three-dimensional coordinate system, which may be called the camera coordinate system. For example, the origin of the camera coordinate system may be at the center of projection of the camera and one axis of the camera coordinate system may be the optical axis of the camera. A camera-image transformation, dependent on intrinsic characteristics of the camera (e.g., focal length, optical center, etc.), may determine how the camera coordinate system is projected onto an image coordinate system referenced to the frame of video 802. The image coordinate system, for example, may be a two-dimensional coordinate system within the plane of the frame of video 802.

Using pose estimation techniques, and based on the frame of video 802, the processing device may calculate the pose of the camera relative to the fiducial marker 606. Using the pose of the camera relative to the fiducial marker 606, the processing device may calculate a marker-camera transformation that quantifies a translation and/or rotation of the camera coordinate system with respect to the marker coordinate system of FIG. 6. The pose estimation techniques may include using known correspondences between points in the marker coordinate system and points in the image coordinate system of the frame of video 802. For example, the processing device may detect coordinates of corners of the fiducial marker 606 in the image coordinate system of the frame of video 802 and already know coordinates of the corners of the fiducial marker 606 in the marker coordinate system. This information, along with the intrinsic characteristics of the camera, may be used by the processing device to calculate the marker-camera transformation. The marker-camera transformation may be, for example, in the form of a matrix or a quaternion.

The marker-camera transformation and the camera-image transformation may determine how to transform the points $O_m$ and $Z_m'$ in the marker coordinate system to points $O_i$ and $Z_i'$ in the image coordinate system. In particular, the points $O_i$ and $Z_i'$ may represent the result of applying the marker-camera transformation and the camera-image transformation to the points $O_m$ and $Z_m'$ (e.g., multiplying the points $O_m$ and $Z_m'$ by the marker-camera transformation and multiplying the result of that multiplication by the camera-image transformation, if the marker-camera transformation and the camera-image transformations are matrices). The processing device may superimpose a directional indicator 814 on the augmented reality display 800 such that the directional indicator 814 is parallel to the direction $\overrightarrow{O_i Z_i'}$. The directional indicator 814 may serve as an instruction for moving the ultrasound imaging device 604 in the superior direction relative to the subject 710.

The direction $\overrightarrow{O_m Z_m}$, prior to rotation and/or tilt of the ultrasound imaging device 604 from the default orientation of FIG. 7, pointed in the superior direction relative to the subject. The direction $\overrightarrow{O_m Z_m'}$, after the rotation and/or tilt of the ultrasound imaging device 604, points in the superior direction relative to the subject. The direction $\overrightarrow{O_i Z_i'}$ appears in the augmented reality to point in the same direction relative to the fiducial marker 606 may therefore appear to point in the superior direction relative to the subject. Accordingly, the directional indicator 814, which appears in the augmented reality display 800 to point parallel to the direction $\overrightarrow{O_i Z_i'}$, may also point in the superior direction relative to the subject and therefore serve as an instruction for moving the ultrasound imaging device 604 in the superior direction relative to the subject. In some embodiments, if the ultrasound imaging device 604 continues to rotate and/or tilt relative to gravity, the directional indicator 814 may not change substantially in response to movement of the ultrasound imaging device using the methods described above. In some embodiments, if the ultrasound imaging device 604 continues to rotate and/or tilt relative to gravity, the directional indicator 814 may be independent of an orientation of the ultrasound imaging device using the methods described above. It should be noted that the points $O_m$, $Z_m$, $O_i$, $Z_i'$, and $Z_i'$ are shown in the above figures for explanatory purposes and may not actually be shown on the augmented reality display 800.

The inventors have also recognized that to avoid directional indicators changing direction as an ultrasound imaging device (e.g., the ultrasound imaging device 200) is rotated or tilted, it may be helpful to fix directional indicators relative to the subject being imaged. In particular, a frame of video of the subject captured by a camera may be used to determine the pose of the camera relative to the subject, and the pose may be used to determine how to how to display, on an augmented reality display showing the frame of video, a directional indicator that appears to point in a particular direction relative to the subject.

Figure 9:
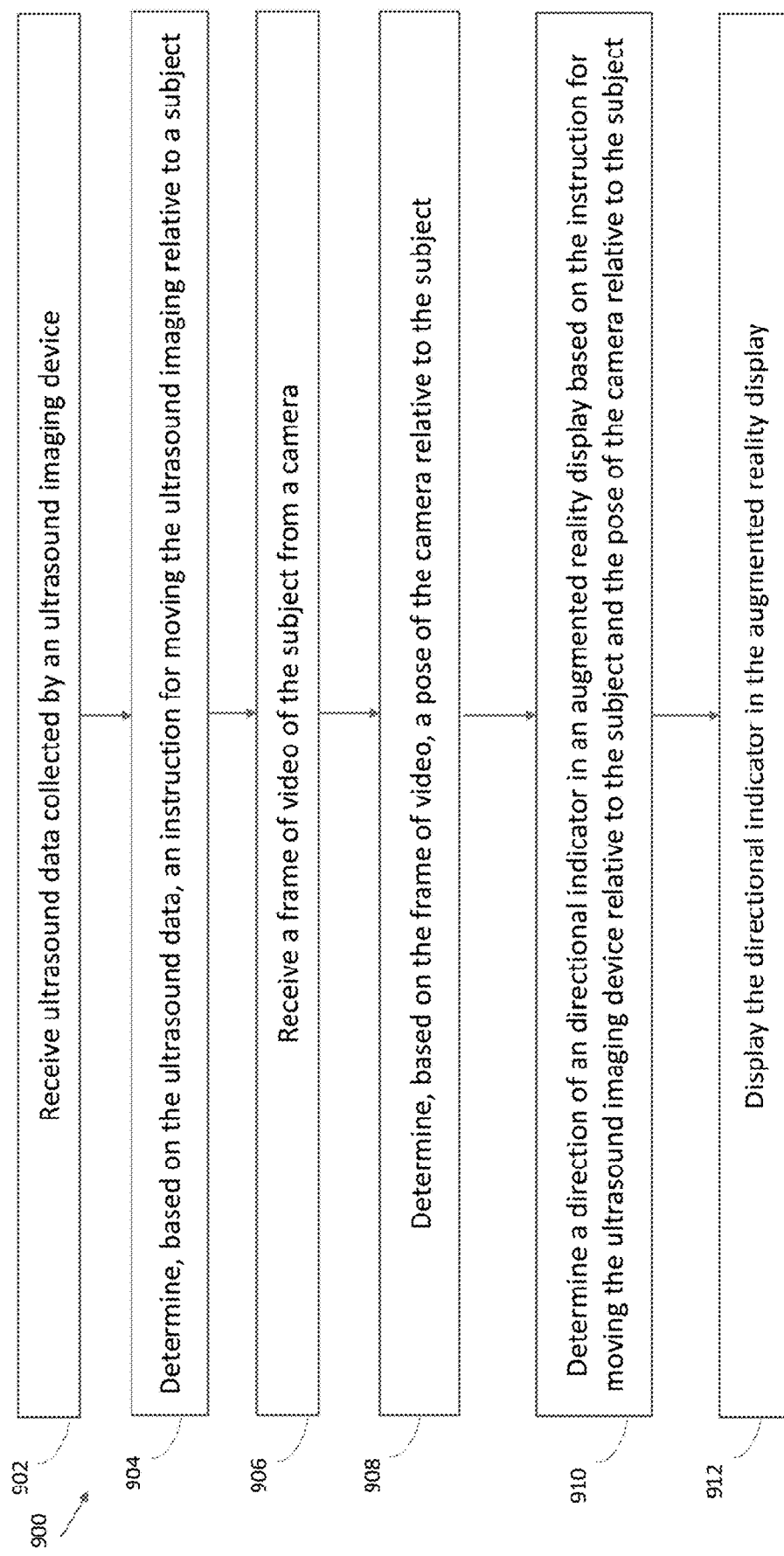
FIG. 9 illustrates an example process for guiding collection of ultrasound, in accordance with certain embodiments described herein.

FIG. 9 illustrates an example process 900 for guiding collection of ultrasound data, in accordance with certain embodiments described herein. In some embodiments, guiding collection of ultrasound data may be performed by displaying, on an augmented reality display, a directional indicator indicating an instruction for moving an ultrasound imaging device (e.g., the ultrasound imaging device 114), where the direction of the directional indicator does not change substantially in response to movement of the ultrasound imaging device. In some embodiments, guiding collection of ultrasound data may be performed by displaying, on an augmented reality display, a directional indicator indicating an instruction for moving an ultrasound imaging device (e.g., the ultrasound imaging device 114), where the direction of the directional indicator does is independent of an orientation of the ultrasound imaging device. The process 900 includes fixing, to a subject being imaged, directional indicators indicating instructions for moving the ultrasound imaging device. The process 900 may be performed by a processing device (e.g., processing device 102) in an ultrasound system (e.g., ultrasound system 100). The processing device may be, for example, a mobile phone, tablet, laptop, or server, and may be in operative communication with the ultrasound imaging device.

In act 902, the processing device receives ultrasound data collected from a subject by the ultrasound imaging device. The ultrasound data may include, for example, raw acoustical data, scan lines generated from raw acoustical data, or ultrasound images generated from raw acoustical data. In some embodiments, the ultrasound imaging device may generate scan lines and/or ultrasound images from raw acoustical data and transmit the scan lines and/or ultrasound images to the processing device. In other embodiments, the ultrasound imaging device may transmit the raw acoustical data to the processing device and the processing device may generate the scan lines and/or ultrasound images from the raw acoustical data. In still other embodiments, the ultrasound imaging device may generate scan lines from the raw acoustical data, transmit the scan lines to the processing device, and the processing device may generate ultrasound images from the scan lines. The ultrasound imaging device may transmit the motion and/or orientation data over a wired communication link (e.g., over Ethernet, a Universal Serial Bus (USB) cable or a Lightning cable) or over a wireless communication link (e.g., over a BLUETOOTH, WiFi, or ZIGBEE wireless communication link) to the processing device. The process 900 proceeds from act 902 to act 904.

In act 904, the processing device determines an instruction for moving the ultrasound imaging device in a particular direction relative to the subject based on the ultrasound data collected in act 902. In some embodiments, the processing device may input the ultrasound data received in act 902 to a statistical model configured to accept ultrasound data and output an instruction for moving the ultrasound imaging device based on the ultrasound data. The instruction may include an instruction for moving the ultrasound imaging device to a target position and/or orientation (e.g., relative to a subject being imaged) and may include any combination of instructions to translate, rotate, and tilt the ultrasound imaging device in a particular direction relative to the subject. For example, the instruction may be to move the ultrasound imaging device in the superior direction relative to the subject. The target position and/or orientation of the ultrasound imaging device may be a position and/or orientation of the ultrasound imaging device relative to a subject such that the ultrasound imaging device can collect a target anatomical view (e.g., a parasternal long axis view of the heart).

In some embodiments, the statistical model may be configured through training to accept ultrasound data and output an instruction for moving the ultrasound imaging device to a target pose based on the ultrasound data. In particular, the statistical model may be trained on sets of training data, where each set of training data includes ultrasound data collected from a subject when the ultrasound imaging device is at a particular pose relative to a subject, and a label indicating an instruction for moving the ultrasound imaging device from the particular pose to the target pose. The training data may be labeled manually by an annotator (e.g., a doctor, sonographer, or other medical professional). The statistical model may thereby learn what instruction to provide based on inputted ultrasound data. The statistical model may be a convolutional neural network, a random forest, a support vector machine, a linear classifier, and/or any other deep learning models. For further description of deep learning models and techniques, see the description with reference to FIG. 13.

In some embodiments, the statistical model may be stored in memory on the processing device and accessed internally by the processing device. In other embodiments, the statistical model may be stored in memory on another device, such as a remote server, and the processing device may transmit the motion and/or orientation data and the ultrasound data to the external device. The external device may input the ultrasound data to the statistical model and transmit the instruction outputted by the statistical model back to the processing device. Transmission between the processing device and the external device may be over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The process 900 proceeds from act 904 to act 906.

In act 906, the processing device receives a frame of video of the subject captured by a camera. In some embodiments, a camera (e.g., camera 106) on the processing device may capture the frame of video. A user of the processing device may hold the ultrasound imaging device on the subject being imaged and position the camera of the processing device (which the user may also be holding) such that the subject is in view of the camera. The process 900 proceeds from act 906 to act 908.

In act 908, the processing device determines, based on the frame of video received in act 906, a pose of the camera relative to the subject. The pose of the camera relative to the subject may be a quantification of a translation and/or rotation of the camera relative to the fiducial marker. In particular, the pose of the camera relative to the subject may be a transformation quantifying a translation and/or rotation of the coordinate system referenced to the camera with respect to a coordinate system referenced to the subject. The transformation may be, for example, in the form of a matrix or a quaternion.

In some embodiments, to determine the pose of the camera relative to the subject, the processing device may input the frame of video received in act 906 to a statistical model configured to accept a frame of video of a subject and output, based on the frame of video, a pose of the camera that collected the frame of video relative to the subject. In some embodiments, the statistical model may be configured through training to accept a frame of video of a subject and output, based on the frame of video, a pose of the camera that collected the frame of video relative to the subject. In particular, the statistical model may be trained on sets of training data, where each set of training data includes a frame of video of a subject and a label indicating a pose of the camera that collected the frame of video relative to the subject. The training data may be labeled manually. The statistical model may thereby learn how to output poses of cameras relative to subjects based on inputted frames of video of the subjects. The statistical model may be a convolutional neural network, a random forest, a support vector machine, a linear classifier, and/or any other deep learning models. For further description of deep learning models and techniques, see the description with reference to FIG. 13.

In some embodiments, the statistical model may be stored in memory on the processing device and accessed internally by the processing device. In other embodiments, the statistical model may be stored in memory on another device, such as a remote server, and the processing device may transmit the frame of video to the external device. The external device may input the frame of video to the statistical model and transmit the pose outputted by the statistical model back to the processing device. Transmission between the processing device and the external device may be over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The process 900 proceeds from act 908 to act 910.

In act 910, the processing device determines the direction of a directional indicator in an augmented reality display. The directional indicator may correspond to the instruction for moving the ultrasound imaging device determined in act 904 by pointing in a direction on the augmented reality display that matches the instruction. For example, if the instruction is to move the ultrasound imaging device in the superior direction relative to the subject, the directional indicator may point in the superior direction relative to the subject. The augmented reality display may include the frame of video of the ultrasound imaging device and a directional indicator superimposed on the frame of video, where the directional indicator corresponds to the instruction for moving the ultrasound imaging device. As will be described further below, the processing device determines the direction of the directional indicator in the augmented reality display based on the instruction for moving the ultrasound imaging device determined in act 904 and the pose of the camera relative to the subject determined in act 908. In some embodiments, the processing device may determine the direction such that the direction of the directional indicator in the augmented reality display does not change substantially in response to movement of the ultrasound imaging device relative to the subject. In some embodiments, the processing device may determine the direction such that the direction of the directional indicator in the augmented reality display is independent of an orientation of the ultrasound imaging device relative to the subject. The processing device may further display the directional indicator in the augmented reality display, either on a display screen included in the processing device (e.g., display screen 108) or on a display screen on another processing device. The process 900 proceeds from act 910 to act 912.

In act 912, the processing device displays the directional indicator in the augmented reality display. The augmented reality display may include the frame of video received in act 506, or a frame of video received later. The directional indicator may be superimposed on the frame of video with the direction determined in act 910. The processing device may display the directional indicator in the augmented reality display either on a display screen included in the processing device (e.g., display screen 108) or on a display screen on another processing device.

Figure 10:
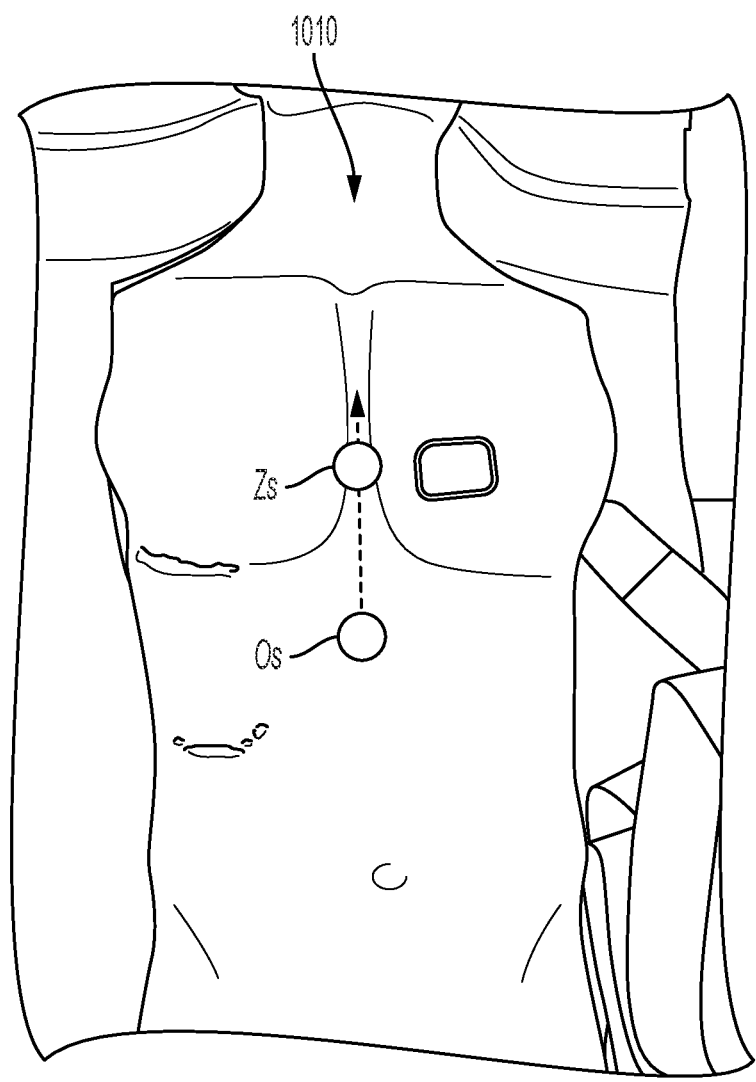
FIG. 10 illustrates an example subject and particular points in a coordinate system referenced to the subject, in accordance with certain embodiments described herein.

FIG. 10 illustrates an example subject 1010. In accordance with certain embodiments described herein, a three-dimensional coordinate system may be referenced to the subject 1010 and may be called the subject coordinate system. For example, the subject coordinate system may be a three-dimensional coordinate system where one axis extends along the superior-inferior direction of the subject, another axis extends along the lateral-medial direction of the subject, and the third axis is orthogonal to a plane formed by these two axes. FIG. 10 further highlights points $O_s$ and $Z_s$, which have particular coordinates in the subject coordinate system. The direction $\overrightarrow{O_s Z_s}$ may point in a particular direction relative to the subject, such as superior to the subject.

Figure 11:
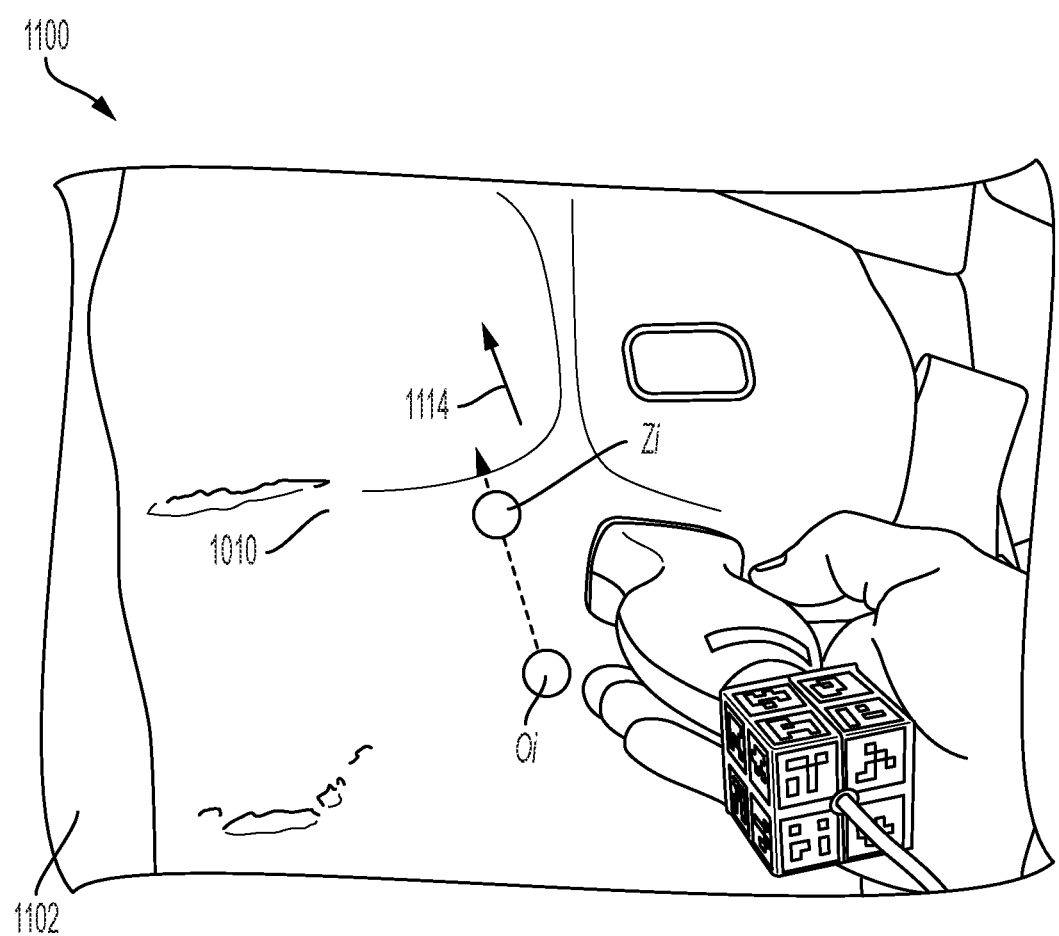
FIG. 11 illustrates an example augmented reality display including a frame of video depicting the subject of FIG. 10, in accordance with certain embodiments described herein.

FIG. 11 illustrates an example augmented reality display 1100 including a frame of video 1102 depicting the subject 1010, in accordance with certain embodiments described herein. The camera that captured the frame of video 1102 may have its own three-dimensional coordinate system, which may be called the camera coordinate system. For example, the origin of the camera coordinate system may be at the center of projection of the camera and one axis of the camera coordinate system may be the optical axis of the camera. A camera-image transformation, dependent on intrinsic characteristics of the camera (e.g., focal length, optical center, etc.), may determine how the camera coordinate system is projected onto an image coordinate system referenced to the frame of video 1102. The image coordinate system, for example, may be a two-dimensional coordinate system within the plane of the frame of video 1102.

As discussed above, the processing device may use a statistical model to determine, from the frame of video 1102, the pose of the camera relative to the subject 1010. Using the pose of the camera relative to the subject 1010, the processing device may calculate a subject-camera transformation that quantifies a translation and/or rotation of the camera coordinate system with respect to the subject coordinate system of FIG. 10. This information may be used by the processing device to calculate the subject-camera transformation. The subject-camera transformation may be, for example, in the form of a matrix or a quaternion.

The marker-camera transformation and the camera-image transformation may determine how to transform the points $O_s$ and $Z_s$ in the subject coordinate system to points $O_i$ and $Z_i$ in the image coordinate system. In particular, the points $O_i$ and $Z_i$ may represent the result of applying the subject-camera transformation and the camera-image transformation to the points $O_s$ and $Z_s$ (e.g., multiplying the points $O_s$ and $Z_s$ by the subject-camera transformation and multiplying the result of that multiplication by the camera-image transformation, if the subject-camera transformation and the camera-image transformations are matrices). The processing device may superimpose a directional indicator 1114 on the augmented reality display 1100 such that the directional indicator 1114 is parallel to the direction $\overrightarrow{O_s Z_s}$.

The direction $\overrightarrow{O_s Z_s}$ points in the superior direction relative to the subject. The direction $\overrightarrow{O_i Z_i}$ appears in the augmented reality display 1100 to point parallel to the direction $\overrightarrow{O_s Z_s}$ and may therefore also point in the superior direction relative to the subject. Accordingly, the directional indicator 1114, which appears in the augmented reality display 1100 to point parallel to the direction $\overrightarrow{O_i Z_i}$, may also point in the superior direction relative to the subject and therefore serve as an instruction for moving the ultrasound imaging device in the superior direction relative to the subject. In some embodiments, if the ultrasound imaging device continues to rotate and/or tilt relative to the subject, the directional indicator 1114 may not change substantially in response to movement of the ultrasound imaging device using the methods described above. In some embodiments, if the ultrasound imaging device continues to rotate and/or tilt relative to the subject, the directional indicator 1114 may be independent of an orientation of the ultrasound imaging device using the methods described above. It should be noted that the points $O_s$, $Z_s$, $O_i$, and $Z_i$ are shown in the above figures for explanatory purposes and may not actually be shown on the augmented reality display 1100.

Figure 12:
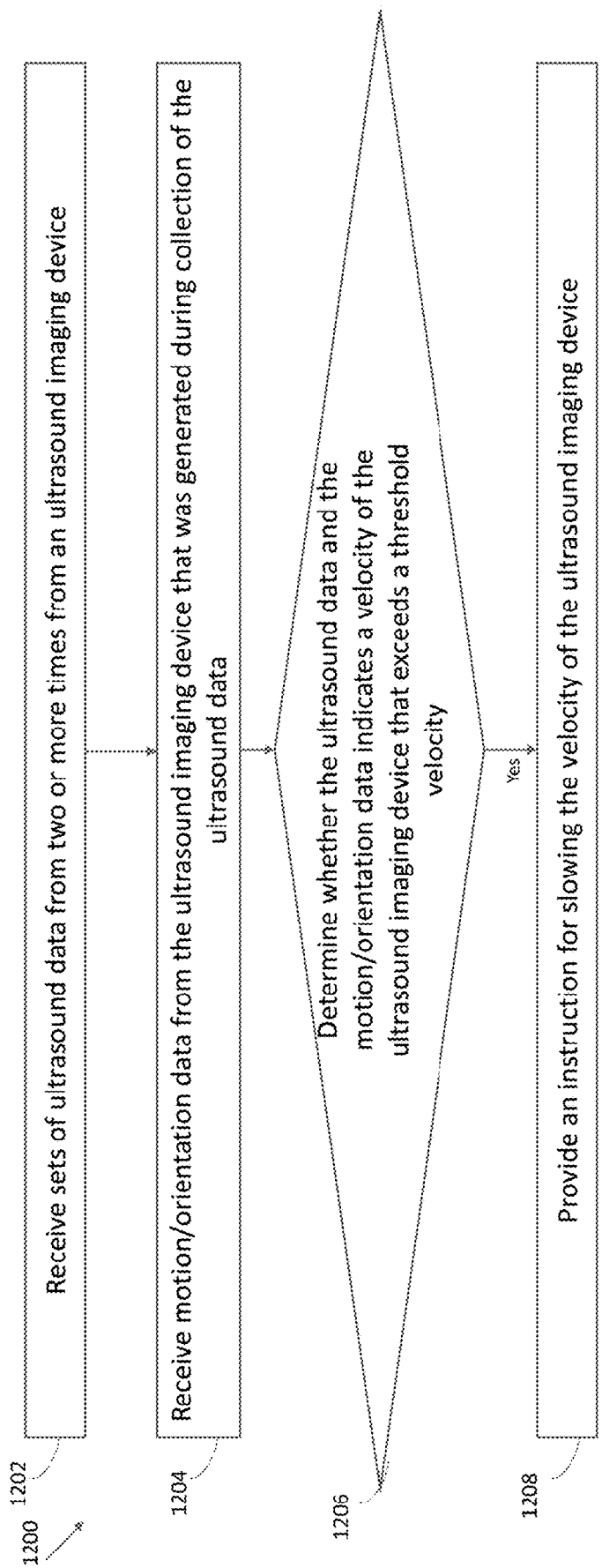
FIG. 12 illustrates an example process for guiding collection ultrasound data by determining whether ultrasound imaging device exceeds a threshold velocity, in accordance with certain embodiments described herein.

FIG. 12 illustrates an example process 1200 for guiding collection of ultrasound data by determining whether the ultrasound imaging device exceeds a threshold velocity, in accordance with certain embodiments described herein. The process 1200 may be performed by a processing device (e.g., processing device 102) in an ultrasound system (e.g., ultrasound system 100). The processing device may be, for example, a mobile phone, tablet, laptop, or server, and may be in operative communication with an ultrasound imaging device (e.g., ultrasound imaging device 114).

In act 1202, the processing devices receives sets of ultrasound data from two or more times from an ultrasound imaging device. For example, the ultrasound data may include a set of ultrasound data collected at one time from one location on a subject and a set of ultrasound data collected at a later time from another location on a subject. The ultrasound data may include, for example, raw acoustical data, scan lines generated from raw acoustical data, or ultrasound images generated from raw acoustical data. In some embodiments, the ultrasound imaging device may generate scan lines and/or ultrasound images from raw acoustical data and transmit the scan lines and/or ultrasound images to the processing device. In other embodiments, the ultrasound imaging device may transmit the raw acoustical data to the processing device and the processing device may generate the scan lines and/or ultrasound images from the raw acoustical data. In still other embodiments, the ultrasound imaging device may generate scan lines from the raw acoustical data, transmit the scan lines to the processing device, and the processing device may generate ultrasound images from the scan lines. The ultrasound imaging device may transmit the ultrasound data over a wired communication link (e.g., over Ethernet, a Universal Serial Bus (USB) cable or a Lightning cable) or over a wireless communication link (e.g., over a BLUETOOTH, WiFi, or ZIGBEE wireless communication link) to the processing device. The process 1200 proceeds from act 1202 to act 1204.

In act 1204, the processing device receives motion and/or orientation data from the ultrasound imaging device that was generated during collection of the ultrasound data in act 1202. For example, the motion and/or orientation data may include data regarding acceleration of the object, data regarding angular velocity of the object, and/or data regarding magnetic force acting on the object (which, due to the magnetic field of the earth, may be indicative of orientation relative to the earth). The ultrasound imaging device may include an accelerometer, a gyroscope, and/or a magnetometer, and these devices may be used by the ultrasound imaging device to generate the motion and/or orientation data. Depending on the devices used to generate the motion and/or orientation data, the motion and/or orientation data may describe three degrees of freedom, six degrees of freedom, or nine degrees of freedom for the ultrasound imaging device. The ultrasound imaging device may transmit the motion and/or orientation data over a wired communication link (e.g., over Ethernet, a Universal Serial Bus (USB) cable or a Lightning cable) or over a wireless communication link (e.g., over a BLUETOOTH, WiFi, or ZIGBEE wireless communication link) to the processing device. The process 1200 proceeds from act 1204 to act 1206.

In act 1206, the processing device determines whether the ultrasound data received in act 1202 and the motion and/or orientation data received in act 1204 indicates a velocity of the ultrasound imaging device that exceeds a threshold velocity. If the processing device determines that the velocity of the ultrasound imaging device exceeds the threshold velocity, the process 1200 proceeds from act 1206 to act 1208. In act 1208, the processing device provides an instruction to the user for slowing the velocity of the ultrasound imaging device. In some embodiments, the processing device may be configured to access a statistical model configured to accept, as inputs, ultrasound data from two or more times collected by an ultrasound imaging device and motion and/or orientation data for the ultrasound imaging device generated during collection of the ultrasound data, and output a velocity of the ultrasound imaging device. To train the statistical model to determine velocity from ultrasound data, the statistical model may be trained on ultrasound data, each set of which is labeled with the time when the ultrasound data was collected and the position of the ultrasound imaging device when it collected the ultrasound data. The statistical model may be able to determine the velocity of the ultrasound imaging device during collection of two sets of ultrasound data based differences in the position and time corresponding to each set of ultrasound data. For example, if one set of ultrasound data was collected at position p1 and time t1 and another set of ultrasound data was collected at position p2 and time t2, the statistical model may determine the velocity of the ultrasound imaging device during collection of the two sets of ultrasound data to be (p1−p2)/(t1−t2). In embodiments in which the motion and/or orientation data includes acceleration data for the ultrasound imaging device, the statistical model may be able to determine the velocity of the ultrasound imaging device by integrating the acceleration data. The statistical model may be able to more accurately determine the velocity of the ultrasound imaging device using both ultrasound data and motion and/or orientation data. In some embodiments, the statistical model may determine the velocity of the ultrasound imaging device based only on ultrasound data. In such embodiments, act 1204 may be absent. In some embodiments, the statistical model may determine the velocity of the ultrasound imaging device based only on motion and/or orientation data. In such embodiments, act 1202 may be absent.

In some embodiments, the processing device may be configured to access another statistical model configured to accept ultrasound data as an input and output an instruction for moving the ultrasound imaging device to a target position and/or orientation based on the ultrasound data. In such embodiments, the processing device may be configured to provide the instruction. The threshold velocity may be related to the lag time between when the ultrasound imaging device collects ultrasound data and when the processing device provides the instruction. In some embodiments, the threshold velocity may be approximately in the range of 0.25 cm/s-2 cm/s, such as 0.25 cm/s, 0.5 cm/s, 0.75 cm/s, 1 cm/s, 1.25 cm/s, 1.5 cm/s, 1.75 cm/s, 2 cm/s, or any other suitable threshold velocity. The inventors have recognized that providing instructions to a user to slow down movement of an ultrasound imaging device when the velocity of the ultrasound imaging device exceeds a threshold velocity may be helpful in providing more accurate instructions for moving the ultrasound imaging device. As another example, if the statistical model has not been trained on sequences of ultrasound images collected by ultrasound imaging devices moving beyond the threshold velocity, the statistical model may not provide accurate instructions based on ultrasound images collected by an ultrasound imaging device moving beyond the threshold velocity. Providing instructions to a user to slow down movement of the ultrasound imaging device may help to increase the accuracy of instructions provided by the statistical model. As another example, moving an ultrasound imaging device too fast may result in blurry ultrasound images, and providing instructions to a user to slow down movement of the ultrasound imaging device may help to improve the quality of ultrasound images collected.

To provide the instruction for slowing the velocity of the ultrasound imaging device, the processing device may display the instruction on a display screen (e.g., display screen 108) of the processing device. For example, if the processing device is a smartphone coupled to the ultrasound imaging device by a cable, the smartphone may display the instruction on its display screen. The displayed instruction may include words (e.g., "Slow down"). In some embodiments, the processing device may generate audio containing the instructions from speakers (e.g., speakers included in the processing device). The instruction provided in act 1208 may be provided in conjunction with the directional indicators displayed in acts 516 and 912. For example, when a user moves the ultrasound imaging device in response to the directional indicators displayed in acts 516 and 912, if the user moves the ultrasound imaging device too fast, the instruction of act 1208 may be provided to slow down movement of the ultrasound imaging device.

In some embodiments, the processing device may determine whether ultrasound data and motion and/or orientation data indicates a velocity of the ultrasound imaging device that is less than a threshold velocity, and if so, provide an instruction to speed up movement of the ultrasound imaging device. This may be helpful if the statistical model has not been trained on sequences of ultrasound images collected by ultrasound imaging devices moving below the threshold velocity, as the statistical model may not provide accurate instructions based on ultrasound images collected by an ultrasound imaging device moving below the threshold velocity. Providing instructions to a user to speed up movement of the ultrasound imaging device may help to increase the accuracy of instructions provided by the statistical model.

The above description has described the processes 500, 900, and 1200 as being performed by a processing device in operative communication with an ultrasound imaging device. However, it should be appreciated that any steps of the processes 500, 900, and 1200 may also be performed by the ultrasound imaging device itself or any combination of devices in operative communication with the ultrasound imaging device and each other. For example, when the process is performed by the ultrasound imaging device 114 itself, the ultrasound imaging device 114 may include the processor 110, the memory 112, the display screen 108, the input device 118, and/or the camera 106. The processor 110 of the ultrasound imaging device 114 may execute one or more processor-executable instructions stored in one or more non-transitory computer-readable storage media (e.g., the memory 112 of the ultrasound imaging device 114), which may serve as non-transitory computer-readable storage media storing processor-executable instructions for execution by the processor 110. Additionally, the embodiments described herein may also be applied to ultrasound devices used for other purposes besides imaging, such as ultrasound devices for treatment (e.g., high-intensity focused ultrasound (HIFU)).

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Aspects of the technology described herein relate to the application of automated image processing techniques to analyze images, such as ultrasound images. In some embodiments, the automated image processing techniques may include machine learning techniques such as deep learning techniques. Machine learning techniques may include techniques that seek to identify patterns in a set of data points and use the identified patterns to make predictions for new data points. These machine learning techniques may involve training (and/or building) a model using a training data set to make such predictions.

Statistical techniques may include those machine learning techniques that employ neural networks to make predictions. Neural networks typically include a collection of neural units (referred to as neurons) that each may be configured to receive one or more inputs and provide an output that is a function of the input. For example, the neuron may sum the inputs and apply a transfer function (sometimes referred to as an "activation function") to the summed inputs to generate the output. The neuron may apply a weight to each input, for example, to weight some inputs higher than others. Example transfer functions that may be employed include step functions, piecewise linear functions, rectified linear unit (ReLu) functions, and sigmoid functions. These neurons may be organized into a plurality of sequential layers that each include one or more neurons. The plurality of sequential layers may include an input layer that receives the input data for the neural network, an output layer that provides the output data for the neural network, and one or more hidden layers connected between the input and output layers. Each neuron in a hidden layer may receive inputs from one or more neurons in a previous layer (such as the input layer) and provide an output to one or more neurons in a subsequent layer (such as an output layer).

A neural network may be trained using, for example, labeled training data. The labeled training data may include a set of example inputs and an answer associated with each input. For example, the training data may include a plurality of ultrasound images or sets of raw acoustical data that are each labeled with an instruction for moving an ultrasound imaging device from the position/orientation where the inputted ultrasound data was collected to a target position/orientation. In this example, the ultrasound images may be provided to the neural network to obtain outputs that may be compared with the labels associated with each of the ultrasound images. One or more characteristics of the neural network (such as the interconnections between neurons (referred to as edges) in different layers and/or the weights associated with the edges) may be adjusted until the neural network correctly classifies most (or all) of the input images.

Once the training data has been created, the training data may be loaded to a database (e.g., an image database) and used to train a neural network using statistical techniques. Once the neural network has been trained, the trained neural network may be deployed to one or more processing devices.

Figure 13:
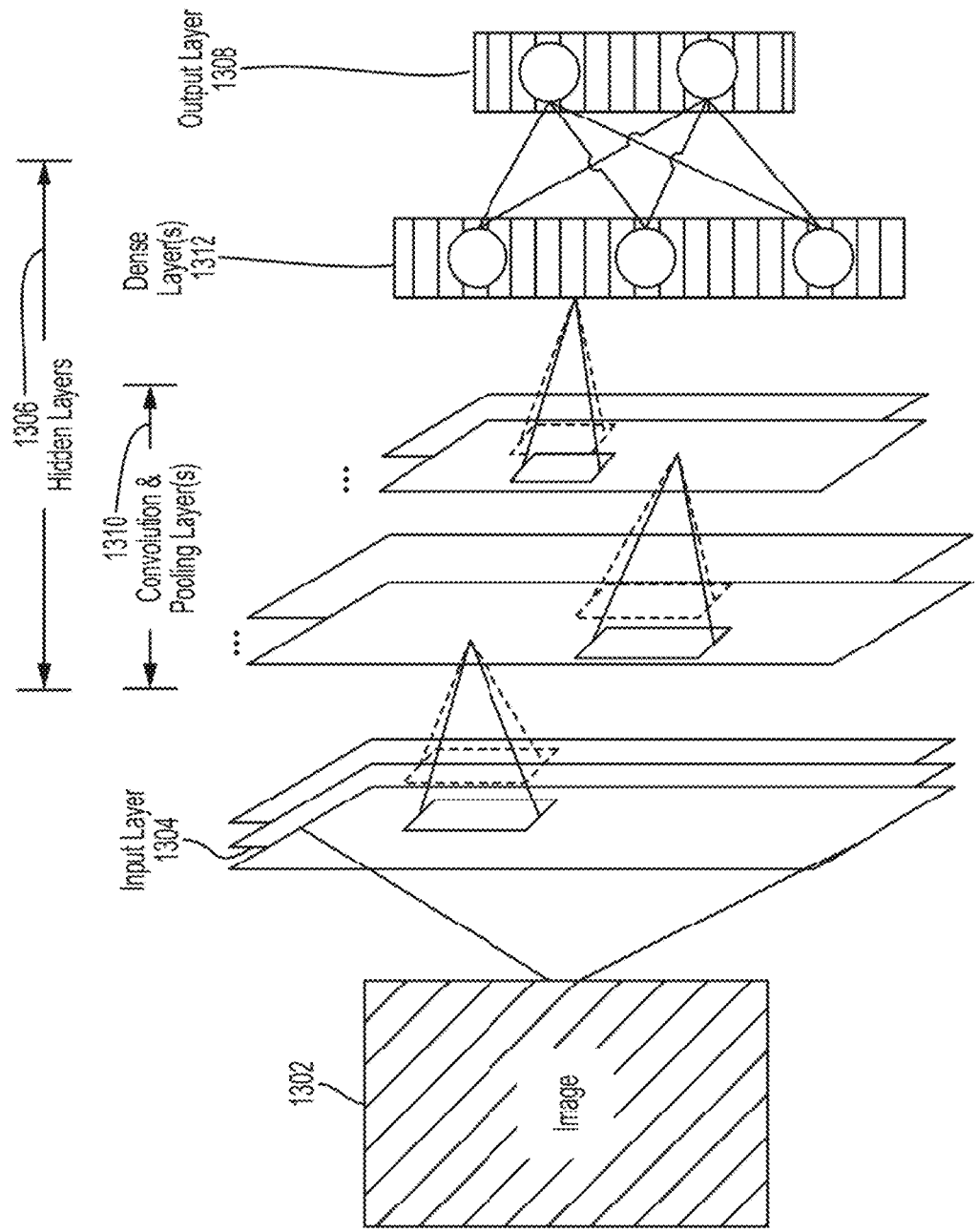
FIG. 13 illustrates an example convolutional neural network that is configured to analyze an image.

In some applications, a neural network may be implemented using one or more convolution layers to form a convolutional neural network. An example convolutional neural network is shown in FIG. 13 that is configured to analyze an image 1302. As shown, the convolutional neural network includes an input layer 1304 to receive the image 1302, an output layer 1308 to provide the output, and a plurality of hidden layers 1306 connected between the input layer 1304 and the output layer 1308. The plurality of hidden layers 1306 includes convolution and pooling layers 1310 and dense layers 1312.

The input layer 1304 may receive the input to the convolutional neural network. As shown in FIG. 13, the input the convolutional neural network may be the image 1302. The image 1302 may be, for example, an ultrasound image.

The input layer 1304 may be followed by one or more convolution and pooling layers 1310. A convolutional layer may include a set of filters that are spatially smaller (e.g., have a smaller width and/or height) than the input to the convolutional layer (e.g., the image 1302). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers 1310 may be followed by dense layers 1312. The dense layers 1312 may include one or more layers each with one or more neurons that receives an input from a previous layer (e.g., a convolutional or pooling layer) and provides an output to a subsequent layer (e.g., the output layer 1308). The dense layers 1312 may be described as "dense" because each of the neurons in a given layer may receive an input from each neuron in a previous layer and provide an output to each neuron in a subsequent layer. The dense layers 1312 may be followed by an output layer 1308 that provides the outputs of the convolutional neural network. The outputs may be, for example, instructions to translate, rotate, and tilt an ultrasound imaging device. The output layer 1308 may provide the outputs to translate, rotate, and tilt the ultrasound imaging device simultaneously and independently of each other. A processing device receiving the outputs from the output layer 1308 may only choose to provide to a user one of these outputs at a time. For example, once the ultrasound imaging device is in a default orientation, the processing device may first provide translation instruction outputs from the neural network, then provide rotation instruction outputs from the neural network once there are no further translation instructions, and then provide tilt instruction outputs from the neural network once there are no further rotation instructions.

It should be appreciated that the convolutional neural network shown in FIG. 13 is only one example implementation and that other implementations may be employed. For example, one or more layers may be added to or removed from the convolutional neural network shown in FIG. 13. Additional example layers that may be added to the convolutional neural network include: a convolutional layer, a transpose convolutional layer, a locally connected layer, a fully connected layer, a rectified linear units (ReLU) layer, a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

For further description of deep learning techniques, see U.S. patent application Ser. No. 15/626,423 titled "AUTOMATIC IMAGE ACQUISITION FOR ASSISTING A USER TO OPERATE AN ULTRASOUND IMAGING DEVICE," filed on Jun. 19, 2017 (and assigned to the assignee of the instant application), which is incorporated by reference herein in its entirety. In any of the embodiments described herein, instead of or in addition to using one or more convolutional neural networks, fully connected neural networks, random forests, support vector machines, linear classifiers, and/or other machine learning models may be used.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
a processing device in operative communication with an ultrasound imaging device, the processing device configured to:
  display, in an augmented reality display, a directional indicator pointing in a particular direction relative to a subject and corresponding to an instruction for moving the ultrasound imaging device relative to the subject in the particular direction;
  determine a change in orientation of the ultrasound imaging device around an axis of gravity from a default orientation; and
  adjust a relationship between the directional indicator and the ultrasound imaging device in the augmented reality display based on the change in orientation of the ultrasound imaging device around the axis of gravity from the default orientation such that the directional indicator in the augmented reality display continues to point approximately in the particular direction relative to the subject;

wherein the default orientation comprises an orientation in which a marker on the ultrasound imaging device faces a default direction relative to the subject.

2. The apparatus of claim 1, wherein the directional indicator in the augmented reality display is displayed so as to appear in the augmented reality display to be part of a real-world environment of the ultrasound imaging device.

3. The apparatus of claim 1, wherein the augmented reality display includes a video captured by a camera on the processing device.

4. The apparatus of claim 1, wherein the processing device is further configured to determine the particular direction relative to the subject for moving the ultrasound imaging device.

5. The apparatus of claim 4, wherein the processing device is configured, when determining the particular direction relative to the subject for moving the ultrasound imaging device, to determine the particular direction using a statistical model.

6. The apparatus of claim 4, wherein the processing device is further configured to receive ultrasound data from the ultrasound imaging device, and wherein the processing device is configured to determine the particular direction for moving the ultrasound imaging device relative to the subject based on the ultrasound data.

* * * * *